US009161715B2

(12) United States Patent
Jung et al.

(10) Patent No.: US 9,161,715 B2
(45) Date of Patent: *Oct. 20, 2015

(54) DETERMINATION OF EXTENT OF CONGRUITY BETWEEN OBSERVATION OF AUTHORING USER AND OBSERVATION OF RECEIVING USER

(75) Inventors: Edward K. Y. Jung, Bellevue, WA (US); Eric C. Leuthardt, St. Louis, MO (US); Royce A. Levien, Lexington, MA (US); Robert W. Lord, Seattle, WA (US); Mark A. Malamud, Seattle, WA (US); John D. Rinaldo, Jr., Bellevue, WA (US); Lowell L. Wood, Jr., Bellevue, WA (US)

(73) Assignee: Invention Science Fund I, LLC, Bellevue, WA (US)

(*) Notice: Subject to any disclaimer, the term of this patent is extended or adjusted under 35 U.S.C. 154(b) by 1454 days.

This patent is subject to a terminal disclaimer.

(21) Appl. No.: 12/157,611

(22) Filed: Jun. 10, 2008

(65) Prior Publication Data

US 2009/0290767 A1   Nov. 26, 2009

Related U.S. Application Data

(63) Continuation-in-part of application No. 12/154,686, filed on May 23, 2008, now Pat. No. 7,904,507.

(51) Int. Cl.
| A61B 5/00 | (2006.01) |
| A61B 5/16 | (2006.01) |
| G06Q 30/02 | (2012.01) |
| G06Q 10/10 | (2012.01) |
| G06F 17/27 | (2006.01) |

(52) U.S. Cl.
CPC . *A61B 5/16* (2013.01); *A61B 5/165* (2013.01); *G06Q 30/02* (2013.01); *G06F 17/27* (2013.01); *G06Q 10/10* (2013.01)

(58) Field of Classification Search
USPC .................................................. 600/300–301
See application file for complete search history.

(56) References Cited

U.S. PATENT DOCUMENTS

| 5,676,138 A * | 10/1997 | Zawilinski ................... 600/301 |
| 5,715,374 A | 2/1998 | Heckerman et al. |
| 5,724,698 A | 3/1998 | Mondragon |
| 5,724,968 A | 3/1998 | Iliff |
| 5,740,549 A | 4/1998 | Reilly et al. |
| 5,761,512 A | 6/1998 | Breslau et al. |
| 6,113,540 A | 9/2000 | Iliff |
| 6,190,314 B1 | 2/2001 | Ark et al. |

(Continued)

OTHER PUBLICATIONS

U.S. Appl. No. 12/215,683, Jung et al.

(Continued)

*Primary Examiner* — William Thomson
*Assistant Examiner* — Bobby Soriano

(57) ABSTRACT

A computationally implemented method includes, but is not limited to: acquiring a result of an observation of an authoring user; acquiring a result of an observation of a receiving user; comparing the result of the observation of the authoring user with the result of the observation of the receiving user; and presenting data indicative of an extent of congruity between the result of the observation of the authoring user and the result of the observation of the receiving user based at least in part on said comparing. In addition to the foregoing, other related method/system aspects are described in the claims, drawings, and text forming a part of the present disclosure.

23 Claims, 12 Drawing Sheets

(56) References Cited

U.S. PATENT DOCUMENTS

| | | | |
|---|---|---|---|
| 6,523,009 B1 | 2/2003 | Wilkins | |
| 6,573,927 B2 | 6/2003 | Parulski et al. | |
| 6,591,296 B1 | 7/2003 | Ghanime | |
| 7,137,070 B2* | 11/2006 | Brown et al. | 715/744 |
| 7,300,402 B2 | 11/2007 | Iliff | |
| 7,406,307 B2 | 7/2008 | Manto | |
| 7,483,899 B2 | 1/2009 | Berry et al. | |
| 7,512,889 B2 | 3/2009 | Newell et al. | |
| 7,529,674 B2 | 5/2009 | Gong et al. | |
| 7,698,255 B2 | 4/2010 | Goodwin et al. | |
| 7,720,784 B1* | 5/2010 | Froloff | 706/47 |
| 7,753,795 B2 | 7/2010 | Harris et al. | |
| 7,933,897 B2 | 4/2011 | Jones et al. | |
| 8,005,984 B2 | 8/2011 | Campbell et al. | |
| 8,495,503 B2* | 7/2013 | Brown et al. | 715/752 |
| 2002/0065836 A1 | 5/2002 | Sasaki | |
| 2002/0095089 A1 | 7/2002 | Yamamoto et al. | |
| 2002/0135618 A1 | 9/2002 | Maes et al. | |
| 2002/0193670 A1 | 12/2002 | Garfield et al. | |
| 2003/0028647 A1 | 2/2003 | Grosu | |
| 2003/0037063 A1 | 2/2003 | Schwartz | |
| 2003/0139654 A1 | 7/2003 | Kim et al. | |
| 2003/0191568 A1 | 10/2003 | Breed | |
| 2003/0196171 A1 | 10/2003 | Distefano, III | |
| 2003/0212546 A1* | 11/2003 | Shaw | 704/9 |
| 2004/0001086 A1* | 1/2004 | Brown et al. | 345/744 |
| 2004/0001090 A1 | 1/2004 | Brown et al. | |
| 2004/0230549 A1 | 11/2004 | Freer et al. | |
| 2004/0236236 A1 | 11/2004 | Yanagidaira et al. | |
| 2005/0010637 A1* | 1/2005 | Dempski et al. | 709/204 |
| 2005/0078804 A1 | 4/2005 | Yomoda | |
| 2005/0283055 A1 | 12/2005 | Shirai et al. | |
| 2006/0010240 A1* | 1/2006 | Chuah | 709/228 |
| 2006/0112111 A1 | 5/2006 | Tseng et al. | |
| 2006/0184464 A1 | 8/2006 | Tseng et al. | |
| 2006/0206833 A1* | 9/2006 | Capper et al. | 715/773 |
| 2006/0221935 A1 | 10/2006 | Wong et al. | |
| 2006/0258914 A1 | 11/2006 | Derchak et al. | |
| 2007/0038054 A1 | 2/2007 | Zhou et al. | |
| 2007/0043590 A1 | 2/2007 | Lee | |
| 2007/0093965 A1 | 4/2007 | Harrison et al. | |
| 2007/0130112 A1 | 6/2007 | Lin | |
| 2007/0192038 A1 | 8/2007 | Kameyama | |
| 2007/0208569 A1* | 9/2007 | Subramanian et al. | 704/270 |
| 2008/0001600 A1 | 1/2008 | deCharms | |
| 2008/0027984 A1* | 1/2008 | Perdomo et al. | 707/104.1 |
| 2008/0059570 A1 | 3/2008 | Bill | |
| 2008/0065468 A1* | 3/2008 | Berg et al. | 705/10 |
| 2008/0096532 A1* | 4/2008 | Lyle et al. | 455/412.1 |
| 2008/0114266 A1 | 5/2008 | Shen et al. | |
| 2008/0120129 A1 | 5/2008 | Seubert et al. | |
| 2008/0139889 A1 | 6/2008 | Bagan | |
| 2008/0146892 A1 | 6/2008 | LeBoeuf et al. | |
| 2008/0162393 A1 | 7/2008 | Iliff | |
| 2008/0162649 A1 | 7/2008 | Lee et al. | |
| 2008/0181381 A1 | 7/2008 | Manto | |
| 2008/0214903 A1 | 9/2008 | Orbach | |
| 2008/0215972 A1* | 9/2008 | Zalewski et al. | 715/706 |
| 2008/0215973 A1* | 9/2008 | Zalewski et al. | 715/706 |
| 2008/0235582 A1* | 9/2008 | Zalewski et al. | 715/716 |
| 2008/0243825 A1 | 10/2008 | Staddon et al. | |
| 2008/0320029 A1 | 12/2008 | Stivoric et al. | |
| 2009/0002178 A1* | 1/2009 | Guday et al. | 340/573.1 |
| 2009/0018832 A1* | 1/2009 | Mukaigaito et al. | 704/251 |
| 2009/0030886 A1 | 1/2009 | Pandeya | |
| 2009/0055484 A1* | 2/2009 | Vuong et al. | 709/206 |
| 2009/0063992 A1* | 3/2009 | Gandhi et al. | 715/752 |
| 2009/0112713 A1* | 4/2009 | Jung et al. | 705/14 |
| 2009/0193344 A1* | 7/2009 | Smyers | 715/753 |
| 2009/0251457 A1* | 10/2009 | Walker et al. | 345/418 |
| 2009/0271375 A1 | 10/2009 | Hyde et al. | |
| 2010/0095362 A1 | 4/2010 | Boberg et al. | |
| 2010/0135369 A1* | 6/2010 | Hagl et al. | 375/219 |

OTHER PUBLICATIONS

U.S. Appl. No. 12/217,131, Jung et al.
U.S. Appl. No. 12/221,253, Jung et al.
U.S. Appl. No. 12/221,197, Jung et al.
U.S. Appl. No. 12/229,517, Jung et al.
U.S. Appl. No. 12/231,302, Jung et al.
Parc Research; "Content-Centric Networking: PARC's Strategy for Pioneering a Self-Organizing Network That Meets Information Needs"; pp. 1-4; Xerox Corporation; located at: http://www.parc.xerox.com/research/projects/networking/contentcentric/mediabackgrounder.html; printed on Mar. 2, 2009.
U.S. Appl. No. 12/931,359, Jung et al.
About.Com.: Email Webpage; printed on Aug. 15, 2008; p. 1 located at http://email.about.com/gi/dynamic/offsite.htm?zi=1/XJ&sdn=email&zu=http%3A%2F%2Fwww.pointofmail.com%2F.
Ambler et al.; "Salience and Choice: Neural Correlates of Shopping Decisions"; Psychology & Marketing; Apr. 2004; pp. 247-261; vol. 21; No. 4; Wiley Periodicals, Inc.
Appenzeller et al.; "The Mobile People Architecture—Technical Report: CSL-TR-99-777"; Jan. 1999; pp. 1-10 (12 pages total incl. title page/abstract and copyright information); located at ftp://reports.stanford.edu/pub/cstr/reports/csl/tr/99/777/CSL-TR-99-777.pdf; Stanford University.
Bergman et al.; "A Personal Email Assistant"; HPInvent Website; printed on Aug. 15, 2008; pp. 1-22 (23 pages total incl. summary page); located at http://www.hpl.hp.com/techreports/2002/HPL-2002-236.pdf; Hewlett-Packard Company 2002.
Cabeza et al.; "Imaging Cognition II: An Empirical Review of 275 PET and fMRI Studies"; Journal of Cognitive Neuroscience; 2000; pp. 1-47; vol. 12; No. 1; Massachusetts Institute of Technology.
Centipaid.Com; "Getting the Best Out of Surgemail's SPAM Features"; bearing dates of 2002-2006 and printed on Aug. 13, 2008; pp. 1-5; located at http://www.centipaid.com/en/support/surgemail.html; Centipaid Corporation.
Chance et al.; "A Novel Method for Fast Imaging of Brain Function, Non-Invasively, With Light"; Optics Express; May 11, 1998; pp. 411-423; vol. 2; No. 10; OSA.
Clearcontext; "User Guide"; bearing dates of 2003-2008 and printed on Aug. 15, 2008; pp. 1-4; located at http://www.clearcontext.com/user_guide/contacts.html; Clearcontext Corporation.
Communigatepro; "CommuniGate® Pro Version 5.1"; bearing dates of 1998-2007 and printed on Aug. 15, 2008; pp. 1-6; located at https://mx2.arl.org/Guide/default.html; Stalker Software, Inc.
Critical Path; "Critical Path: Putting Mobile Email in Context"; bearing a date of Aug. 11, 2005 and printed on Aug. 13, 2008; pp. 1-2; located at http://www.cbronline.com/article_feature.asp?guid=D9E4E0B0-BE6A-4928-8857-3A3682D852C1; CBR and CBRonline.com.
Goodmail Systems; "Certified Email: How it Works"; printed on Aug. 13, 2008; p. 1; located at http://www.goodmailsystems.com/products/certified-email/how_it_works.php.
Huang et al.; "MapWeb: A Location-Based Converged Communications Platform"; Bell Labs Technical Journal—Lucent Technologies Inc.; 2006; pp. 159-171; Wiley Periodicals, Inc.
Inovalive; "iNovaLive: Email Solutions Through Email Evolution website"; bearing a date of 2006 and printed on Aug. 15, 2008; pp. 1-2; located at http://inovalive.com/site/index; iNovaSoft Ltd.
Kenning et al.; "NeuroEconomics: An Overview from an Economic Perspective"; Brain Research Bulletin; 2005; pp. 343-354; vol. 67; Elsevier Inc.
Lee et al.; "What is 'Neuromarketing'? A Discussion and Agenda for Future Research"; International Journal of Psychophysiology; bearing dates of 2006 and 2007; pp. 199-204; vol. 63; Elsevier B.V.
Matthews et al.; "Applications of fMRI in Translational Medicine and Clinical Practice"; Nature Reviews/Neuroscience; Sep. 2006; pp. 732-744; vol. 7; Nature Publishing Group.
Murphy, Kevin; "Pay-Per-Email Scheme Draws Critics"; bearing a date of Feb. 7, 2006 and printed on Aug. 13, 2008; pp. 1-3; located at http://www.cbronline.com/article_news.asp?guid=A921B4EA-A489-4B5C-8053-423F46499767; CBR and CBRonline.com.

(56) References Cited

OTHER PUBLICATIONS

Nedos et al.; "LATTE: Location and Time Triggered Email"; pp. 1-14; located at https://www.cs.tcd.ie/publications/tech-reports/reports.04/TCD-CS-2004-32.pdf; Trinity College, Dublin, Ireland.

Parc Research; "Content Centric Networking"; bearing dates of 2002-2007; printed on Aug. 15, 2008; pp. 1-2; located at http://www.parc.xerox.com/research/projects/networking/contentcentric/default.html; Palo Alto Research Center Incorporated.

Pointofmail.Com.; "Advanced Email Experience™"; bearing dates of 1999-2008 and printed on Aug. 15, 2008; p. 1; located at http://email.about.com/gi/dynamic/offsite.htm?zi=1/XJ&sdn=email&zu=http%3A%2F%2Fwww.readnotify.com%2F.

Roecker et al.; "Context-Dependent Email Notification Using Ambient Displays and Mobile Devices"; 2005; pp. 137-138; located at http://ieeexplore.ieee.org/iel5/10045/32238/01505288.pdf?tp=&isnumber=32238&arnumber=1505288; IEEE.

Techcrunch.Com; "Seriosity to Fix Email Overload (Or Not)" blog; bearing a date of Feb. 28, 2007 and printed on Aug. 13, 2008; pp. 1-12; located at http://www.techcrunch.com/2007/02/28/seriosity-to-fix-email-overload-or-not/all-comments/#comments.

Terdiman, Daniel; "A Cure for E-Mail Attention Disorder?"; CNET News.com; Feb. 28, 2007 and printed on Aug. 13, 2008; pp. 1-4; located at http://news.com.com/2100-1038_3-6162798.html; CNET Networks, Inc., a CBS Company.

Tschabitscher, Heinz; "BigString.com—Free Email Service"; About.com: Email; printed on Aug. 13, 2008; pp. 1-2; located at http://email.about.com/od/freeemailreviews/gr/bigstring_com.htm.

Tschabitscher, Heinz; "Confimax—Certified Email Service"; About.com: Email; printed on Aug. 13, 2008; pp. 1-2; located at http://email.about.com/cs/oepluginreviews/gr/confimax.htm.

Tschabitscher, Heinz; "DidTheyReadIt—Certified Email Service"; About.com: Email; printed on Aug. 13, 2008; pp. 1-2; located at http://email.about.com/od/windowsreturnreceipts/gr/didtheyreadit.htm.

Tschabitscher, Heinz; "E-mail Secure—Certified Email Service"; About.com: Email; printed on Aug. 13, 2008; pp. 1-2; located at http://email.about.com/od/windowsreturnreceipts/gr/e_mailsecure.htm.

Tschabitscher, Heinz; "Pointofmail 5.5—Certified Email Service"; About.com: Email; printed on Aug. 13, 2008; pp. 1-2; located at http://email.about.com/od/windowsreturnreceipts/ar/pointofmail.htm.

Tschabitscher, Heinz; "ReadNotify—Certified Email Service"; About.com: Email; printed on Aug. 13, 2008; pp. 1-2; located at http://email.about.com/od/windowsreturnreceipts/gr/readnotify.htm.

Twitter.Com website located at http://twitter.com; [No document provided].

Westen et al.; "Neural Bases of Motivated Reasoning: An fMRI Study of Emotional Constraints on Partisan Political Judgment in the 2004 U.S. Presidential Election"; Journal of Cognitive Neuroscience; 2006; pp. 1947-1958; vol. 18; No. 11; Massachusetts Institute of Technology.

U.S. Appl. No. 13/135,462, Jung et al.

* cited by examiner

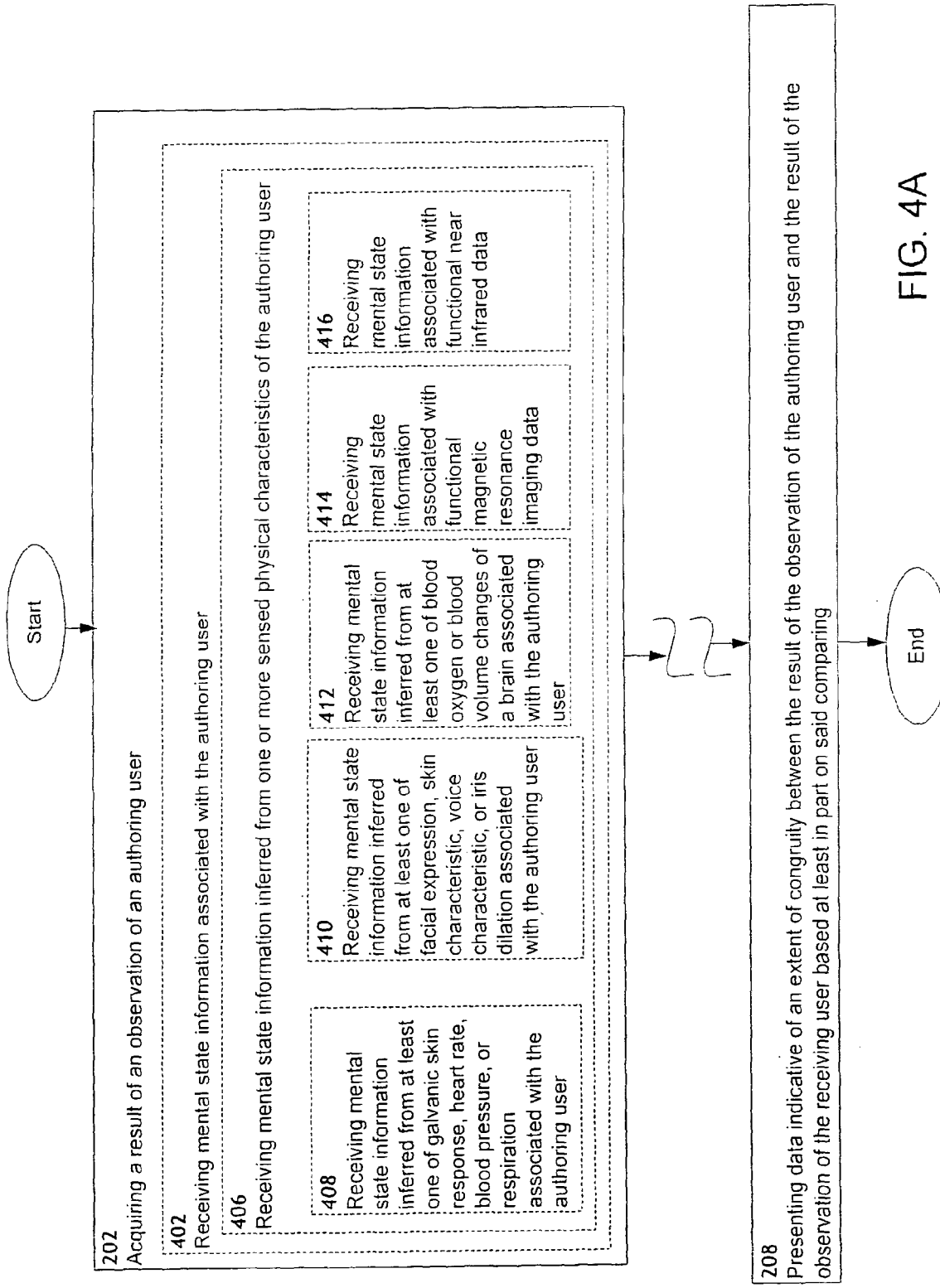

DETERMINATION OF EXTENT OF CONGRUITY BETWEEN OBSERVATION OF AUTHORING USER AND OBSERVATION OF RECEIVING USER

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 12/154,686, entitled DETERMINATION OF EXTENT OF CONGRUITY BETWEEN OBSERVATION OF AUTHORING USER AND OBSERVATION OF RECEIVING USER, naming Edward K. Y. Jung, Eric C. Leuthardt, Royce A. Levien, Robert W. Lord, Mark A. Malamud, John D. Rinaldo, Jr. and Lowell L. Wood, Jr., as inventors, filed 23, May, 2008 now U.S. Pat. No. 7,904,507, which is currently co-pending, or is an application of which a currently co-pending application is entitled to the benefit of the filing date.

For purposes of the USPTO extra-statutory requirements, the present application is related to U.S. patent application Ser. No. 12/284,348, entitled ACQUISITION AND PARTICULAR ASSOCIATION OF INFERENCE DATA INDICATIVE OF INFERRED MENTAL STATES OF AUTHORING USERS, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 19 Sep. 2008, which is currently co-pending, or is an application of which a currently co-pending application is entitled to the benefit of the filing date.

For purposes of the USPTO extra-statutory requirements, the present application is related to U.S. patent application Ser. No. 12/284,710, entitled ACQUISITION AND PARTICULAR ASSOCIATION OF INFERENCE DATA INDICATIVE OF INFERRED MENTAL STATES OF AUTHORING USERS, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 23 Sep. 2008, which is currently co-pending, or is an application of which a currently co-pending application is entitled to the benefit of the filing date.

For purposes of the USPTO extra-statutory requirements, the present application is related to U.S. patent application Ser. No. 12/287,687, entitled ACQUISITION AND PRESENTATION OF DATA INDICATIVE OF AN EXTENT OF CONGRUENCE BETWEEN INFERRED MENTAL STATES OF AUTHORING USERS, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 10 Oct. 2008, which is currently co-pending, or is an application of which a currently co-pending application is entitled to the benefit of the filing date.

For purposes of the USPTO extra-statutory requirements, the present application is related to U.S. patent application Ser. No. 12/288,008, entitled ACQUISITION AND PRESENTATION OF DATA INDICATIVE OF AN EXTENT OF CONGRUENCE BETWEEN INFERRED MENTAL STATES OF AUTHORING USERS, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 14 Oct. 2008, which is currently co-pending, or is an application of which a currently co-pending application is entitled to the benefit of the filing date.

SUMMARY

A computationally implemented method includes, but is not limited to: acquiring a result of an observation of an authoring user; acquiring a result of an observation of a receiving user; comparing the result of the observation of the authoring user with the result of the observation of the receiving user; and presenting data indicative of an extent of congruity between the result of the observation of the authoring user and the result of the observation of the receiving user based at least in part on said comparing. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

A computationally implemented system includes, but is not limited to: means for acquiring a result of an observation of an authoring user; means for acquiring a result of an observation of a receiving user; means for comparing the result of the observation of the authoring user with the result of the observation of the receiving user; and means for presenting data indicative of an extent of congruity between the result of the observation of the authoring user and the result of the observation of the receiving user based at least in part on said comparing. In addition to the foregoing, other system aspects are described in the claims, drawings, and text forming a part of the present disclosure.

A computationally implemented system includes, but is not limited to: circuitry for acquiring a result of an observation of an authoring user; circuitry for acquiring a result of an observation of a receiving user; circuitry for comparing the result of the observation of the authoring user with the result of the observation of the receiving user; and circuitry for presenting data indicative of an extent of congruity between the result of the observation of the authoring user and the result of the observation of the receiving user based at least in part on said comparing. In addition to the foregoing, other system aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 4A is a high-level logic flowchart of a process depicting alternate implementations of the acquisition operation 202 of FIG. 2.

DETAILED DESCRIPTION

Figure 1A:
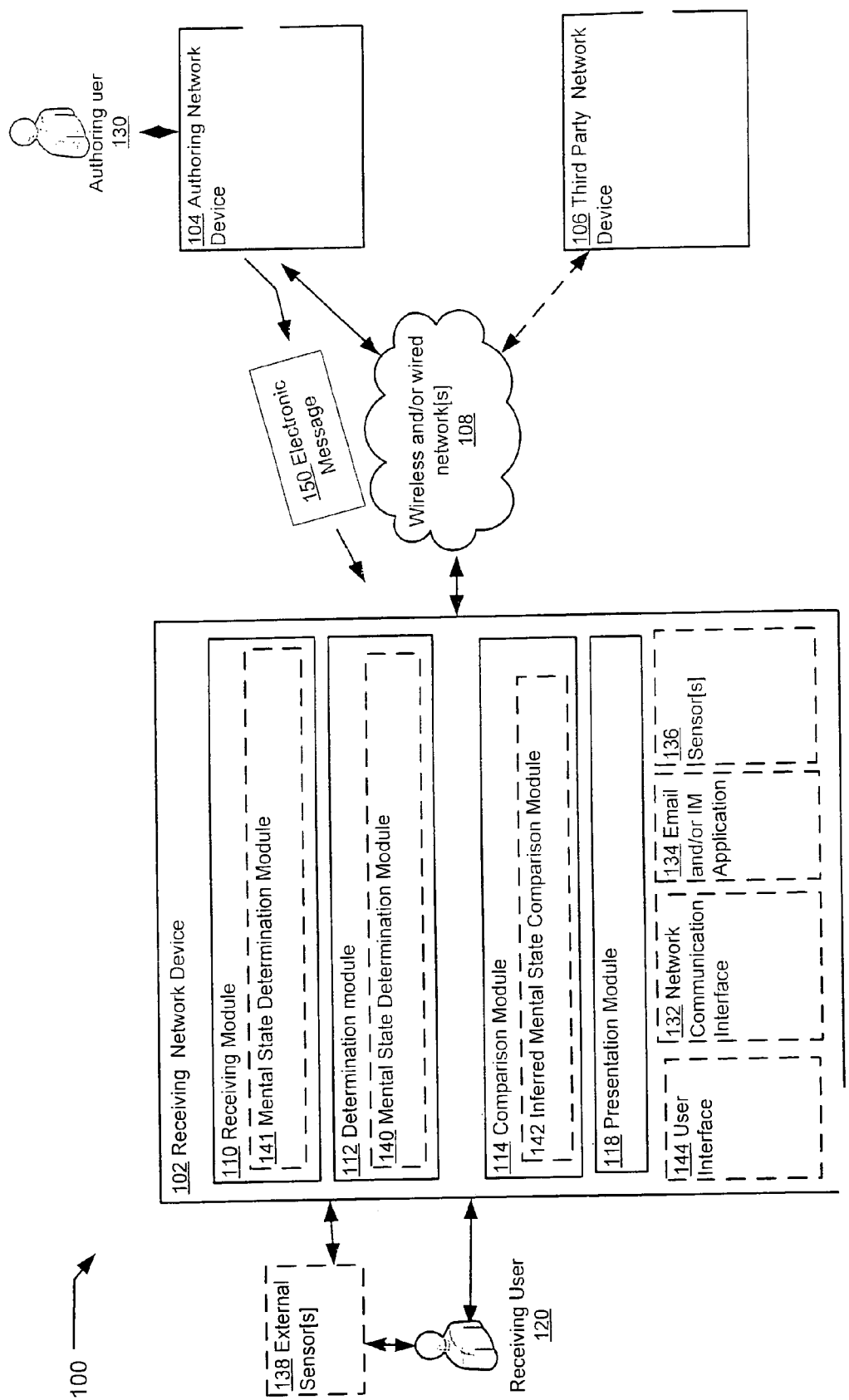
FIG. 1A shows a high-level block diagram of a network device operating in a network environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1A illustrates an example environment in which one or more aspects of various embodiments may be implemented. In the illustrated environment, an exemplary system 100 may include at least a receiving user network device (herein "receiving network device") 102 to be used by a receiving user 120. In some implementations, the receiving network device 102 may be used in order to provide an indication that the receiving user 120 correctly understands the meaning and/or tone of electronic messages (e.g., electronic message 150) authored and sent by, for example, an authoring user 130. In other words, whether a receiving user 120 "gets" electronic messages (e.g., email, instant message (IM), or voice message) sent by an authoring user 130.

For example, if authoring user 130 composes and sends an electronic message containing a humorous story to the receiving user 120 with the intent to lighten the mood of the receiving user 120, the receiving network device 102 may be advantageously designed to determine and indicate whether the receiving user 120 when reading the electronic message is misunderstanding the tone and/or meaning of the electronic message (e.g., the receiving user 120 becomes mistakenly distressed by the electronic message because the receiving user 120 misunderstands the tone of the message). In some instances, this may be accomplished by comparing the mental state of the authoring user 130 during the composition or drafting of the electronic message 150 by the authoring user 130 and the mental state of the receiving user 120 when the resulting electronic message 150 is being displayed to the receiving user 120. The results of the comparison may then be displayed to the receiving user 120 and/or provided to a third party participant network device 106 to indicate that the user "got" the electronic message. These and other aspects of various embodiments will be described in greater detail herein.

Returning to FIG. 1A and as depicted, the receiving network device 102 may communicate with an authoring user network device (herein "authoring network device") 104, and in some instances, may also communicate with a third party participant network device (herein "third party network device") 106 via a wireless and/or wired network[s] 108. The receiving network device 102 may be any type of computing or communication device such as a personal computer (PC), a laptop computer, a personal digital assistant (PDA), a cellular telephone, a blackberry, and so forth.

The receiving network device 102 may include various components including, for example, a receiving module 110 for acquiring a result of an observation of the authoring user 130 including in some instances, for example, observations of physical characteristics of the authoring user 130 and/or the inferred mental state of the authoring user 130 during composition or proximate to the composition of an electronic message by the authoring user 130. The receiving network device 102 may further include a determination module 112 for acquiring a result of an observation (e.g., physical characteristics) of the receiving user 120. In some implementations, the determination module 112 may further include a mental state determination module 140 for determining at least one inferred mental state of the receiving user 120 based, at least in part, on the observations of physical characteristics of the receiving user 120 during or proximate to when the electronic message sent by the authoring user 130 is being displayed to or read by the receiver user 120. The receiving network device 102 may also include a comparison module 114 for comparing the result of the observation of the authoring user 130 with the result of the observation of the receiving user 120, and a presentation module 118 for presenting data indicative of an extent of congruity between the result of the observation of the authoring user and the result of the observation of the receiving user based at least in part on the comparison made by the comparison module 114.

The receiving network device 102 may be further endowed with a network communication interface 132 for interfacing with, for example, a wireless and/or wired network or networks 108, an email and/or instant message (IM) application 134 for receiving and transmitting email and/or IM messages, a user interface 144 including, for example, display, touchscreen, keypad, speaker system, and so forth, and one or more sensors 136 for monitoring or measuring physical and physiological characteristics of the receiving user 120. In some implementations, the sensors 136 may be integrated with the receiving network device 102 while in other implementations, one or more sensors may be external sensors 138.

Examples of sensors 136 that may be employed by receiving network device 102 include, for example, devices that can measure brain activities such as a functional near-infrared imaging (fNIR) device, a functional magnetic resonance imaging (fMRI) device, a magnetoencephalography (MEG) device, an electroencephalography (EEG) device, and/or a positron emission topography device. These devices may measure a variety of physiological parameters that may be processed in order to determine the mental state of a subject (e.g., receiving user 120). Other types of sensors such as those that measure other types of physical or physiological characteristics may be employed as sensors 136/138. For example, in some implementations, the sensor[s] 136/138 may include an iris response device, a gaze tracking device, a skin response device (e.g., galvanic skin sensor), and/or a voice response device. In some alternative implementations, the receiving network device 102 may be wirelessly (e.g., wireless personal area network (WPAN), wireless local area network (WLAN), and so forth) and/or wired connected to one or more external sensors 138.

Data obtained from observations made with one or more such sensors 136/138 may be used by, for example, the mental state determination module 140 in order to determine an inferred mental state of the receiving user 120 including, for example, preference, trust, fear, happiness, fear, pain, distress, anger, deception, fairness or unfairness, frustration, approval and disapproval, degree of attention, memory usage—both short and long term, of the receiving user. For example, data obtained from an fNIR device 136/138 may indicate that a subject or a user is in at least one of a state of anger, a state of distress, or a state of pain. Data obtained from other types of sensors 136/138 may indicate that a user is in a state of frustration, a state of approval or disapproval, a state of trust, a state of fear, or a state of happiness.

Figure 1B:
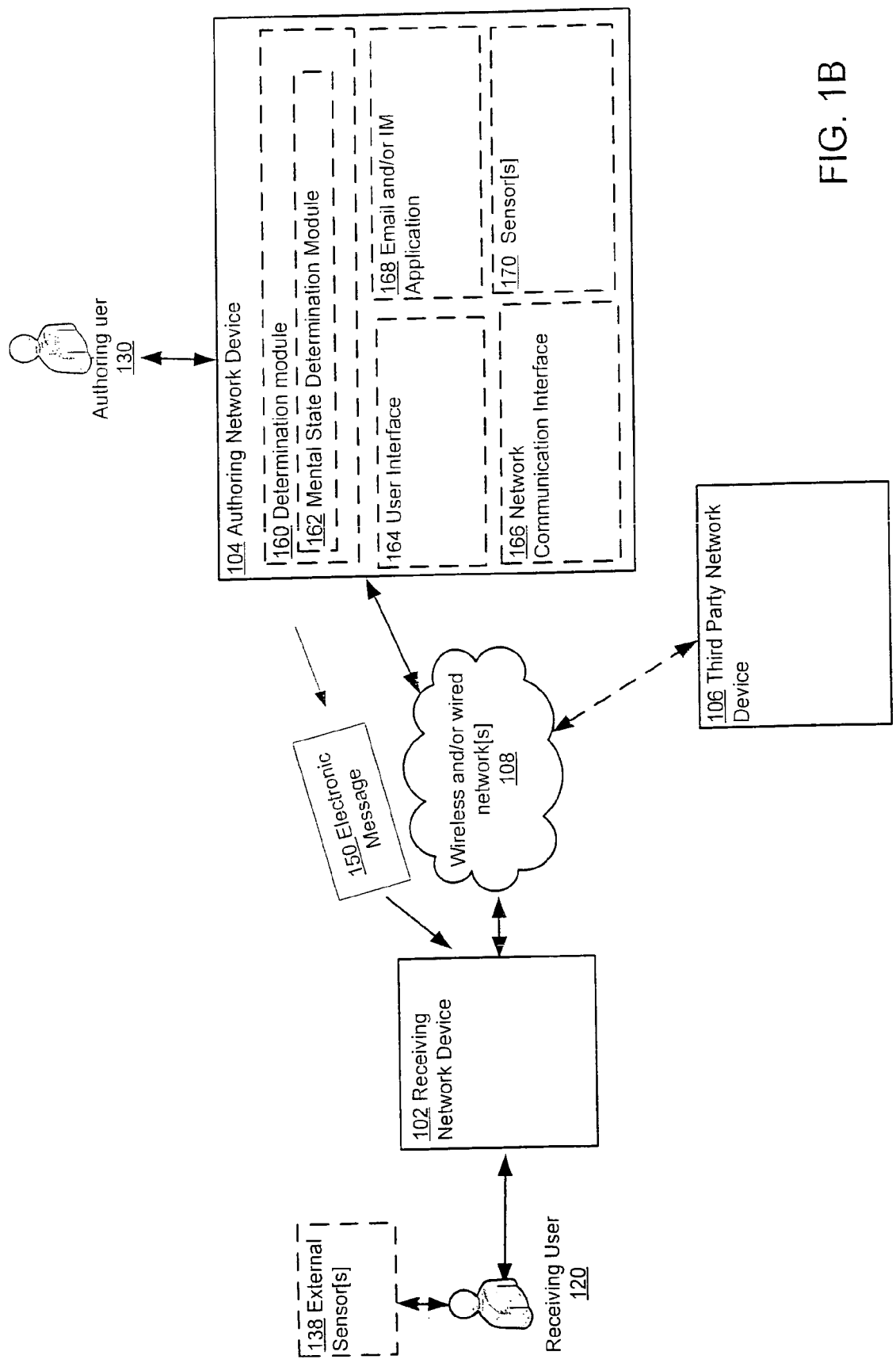
FIG. 1B shows another perspective of the network environment of FIG. 1A.

In order to appreciate various aspects of the receiving network device 102, the following illustrative example is provided. In this example, the authoring user 130 using the authoring network device 104 may initially compose an electronic message 150 to the receiving user 120. Turning now to FIG. 1B, which is another perspective of the exemplary environment depicted in FIG. 1A. More particularly, FIG. 1B shows that the authoring network device 104 includes some of the same components included in the receiving network device 102 illustrated in FIG. 1A. For instance, and as depicted in FIG. 1B, the authoring network device 104 includes a determination module 160, which may further include a mental state determination module 162, a user interface 164, a network communication interface 166, an email and/or IM application 168, and one or more sensors 170.

The electronic message 150 to be sent to the receiving network device 102 may be in a form of an email message, an IM message, a voice message, or another type of electronic message. During the composition of the electronic message 150, the authoring network device 104, which may be endowed with one or more sensors 170, may observe physical or physiological (herein "physical") characteristics of the authoring user 130 during or proximate to the composition of the electronic message 150. Based on the observation of the physical characteristics, the authoring network device 104, and more particularly, the mental state determination module 162, may infer one or more mental states of the authoring user 130. The mental state determination module 162 (as well as the mental state determination modules 140 and 141 of receiving network device 102 of FIG. 1A) may employ different techniques in order to infer one or more mental states from observed physical characteristics. In some implementations, this may mean associating particular physical characteristics or patterns of physical characteristics to one or more mental states (i.e., inferred mental states).

For example, if the one or more sensors 170 depicted in FIG. 1B include an fMRI device, then the fMRI device may be used in order to scan the brain of the subject (e.g., authoring user 130) during or proximate to the composition of the electronic message 150 by the authoring user 130. As a result of the functional magnetic resonance imaging procedure performed using the fMRI device; the fMRI device may provide a profile or a pattern of brain activities (e.g., oxygen and/or blood flow) of the authoring user 130. The determined "brain activity pattern" may then be compared to brain activity patterns that may be stored in a database or library. Such a database or library may contain numerous brain activity patterns that may have been obtained by sampling a number of people from the general population, having, for example, similar metrics as the authoring user 130 (e.g., age, gender, race, education, and so forth). By asking each sampled person what they felt (e.g., mental state) at the time when their brain activity pattern was recorded, each brain activity pattern stored in the library or database may be associated with one or more mental states. As a result, by comparing the determined brain activity pattern of the authoring user 130 with the brain activity patterns stored in the database or library, one or more mental states may be inferred from the observed physical characteristics of the authoring user 130.

The inferred one or more mental states may then be provided to the receiving network device 102 by, for example, attaching data indicative of the determined inferred one or more mental states onto the electronic message 150 being sent. Alternatively, instead of providing the one or more inferred mental states of the authoring user 130, the authoring networking device 104 may provide "raw" data obtained from the observations of the physical characteristics (e.g., using sensors 170) of the authoring user 130 to the receiving network device 102. For example, in some implementations, the authoring network device 104 may provide to the receiving network device 102 data indicating the physical characteristics (e.g., brain activity) observed or measured by a sensor 170 (e.g., fNIR device) rather than an inferred mental state determined by the mental state determination module 162. In this particular implementation, the receiving network device 102 (e.g., using an mental state determination module 141 or similar such module disposed in the receiving module 110) may then process the raw data obtained from the authoring network device 104 to determine an inferred mental state or states of the authoring user 130 during or proximate to the composition of the electronic message.

The receiving module 110 of the receiving network device 102, as depicted in FIG. 1A, may initially receive the electronic message 150 composed by authoring user 130 as well as the inferred mental state (or the result of the observation of the physical characteristics) of the authoring user 130. In particular, the receiving module 110 in some implementation may employ the network communication interface 132 and the email and/or IM application 132 in order to receive and process the electronic message 150. Alternatively, if the electronic message 150 is in the form of an audio or voice message, then an audio application (e.g., voice over internet-protocol (VoIP) application) may be employed instead of the email and/or IM application 132.

If the received results of the observation of the physical characteristics of the authoring user 130 are in the form of raw data from sensors 170 instead of in the form of an inferred mental state of the authoring user 130, then the received results may be processed by, for example, a mental state determination module 141, in order to obtain an inferred mental state of the authoring user 130 during or proximate to the composition of the electronic message. The term "proximate" as used herein may refer to, in some instances, partly during, immediately subsequent, or immediately preceding the composition of the electronic message 150. Note that in the embodiment depicted in FIG. 1A, both the receiving module 110 and the determination module 112 of receiving network device 102 may each include a mental state determination module 140 and 141, respectively, which in some implementations, may be the same mental state determination module 140/141.

After receiving the electronic message 150 from the authoring network device 104, the receiving network device 102 may present or display the electronic message 150 to the receiving user 120 via the user interface 144. During or proximate to the presentation of the electronic message 150 to the receiving user 120, the determination module 112 may make an observation of the physical characteristics of the receiving user 120 using one or more sensors 136/138. In some implementations, the mental state determination module 140 may determine an inferred mental state for the receiving user 120 based, at least in part, on the results of the observation of the physical characteristic of the receiving user 120.

In some implementations, the observation of the physical characteristics of the receiving user 120 may be made by using one or more sensors 136/138. For example, in some embodiments, multiple sensors 136/138 such as a combination of a galvanic skin sensor, an iris response device, a gaze tracking device, and/or a voice response device may be used in order to observe various physical characteristics of the receiving user 120 when the electronic message 150 is being viewed by the receiving user 120. Based on the observations made by the multiple sensors 136/138, the sensors 136/138 may output raw data indicating the physical characteristics of the receiving user 120. Such raw data may include, for example, galvanic skin response data provided by a galvanic skin sensor and a gaze tracking data obtained from a gaze tracking device. The raw data may then be used by the mental state determination module 140 in order to infer one or more mental states for the receiving user 120.

The comparison module 114, in some instances, may then compare the results of the observation (e.g., inferred mental state) of the authoring user 130 with the results of the observation (e.g., inferred mental state) of the receiving user 120. Based on this comparison, the presentation module 118 may present an extent of congruity between the result of the observation of the authoring user 130 and the result of the observation of the receiving user 120 to the receiving user 120 and/or to the third party network device 106.

The various components (e.g., receiving module 110, determination module 112, comparison module 114, presentation module 118, network communication interface 132, email and/or IM application 134, and so forth) included with the receiving network device 102 of FIG. 1 may be embodied by hardware, software and/or firmware. For example, in some implementations the receiving module 110, the determination module 112, the comparison module 114, the presentation module 118, and their sub-modules, may be implemented with a processor (e.g., microprocessor, controller, and so forth) executing computer readable instructions (e.g., computer program product) stored in a storage medium (e.g., volatile or non-volatile memory) such as a signal-bearing medium. Alternatively, hardware such as application specific integrated circuit (ASIC) may be employed in order to implement such modules in some alternative implementations.

Figure 2:
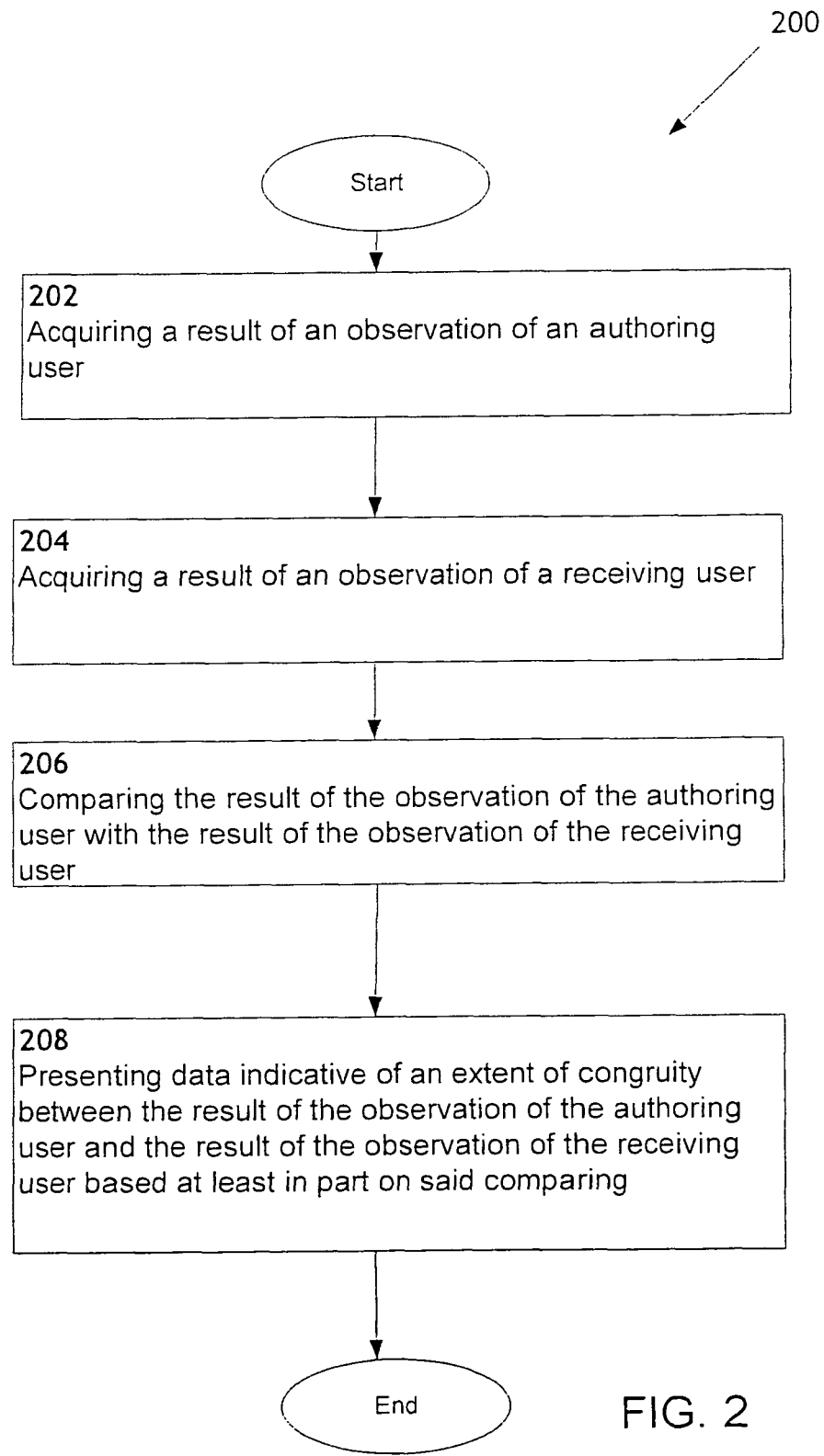
FIG. 2 is a high-level logic flowchart of a process.

FIG. 2 illustrates an operational flow 200 representing example operations related to presentation of extent of congruity between the result of an observation of an authoring user and the result of an observation of a receiving user. In FIG. 2 and in the following figures that include various examples of operational flows, discussion and explanation may be provided with respect to the above-described examples of FIG. 1, and/or with respect to other examples and contexts. However, it should be understood that the operational flows may be executed in a number of other environments and contexts, and/or in modified versions of FIG. 1A. Also, although the various operational flows are presented in the sequence(s) illustrated, it should be understood that the various operations may be performed in other orders than those which are illustrated, or may be performed concurrently.

Further, in FIG. 2 and in following figures, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

After a start operation, the operational flow 200 may move to an acquisition operation 202, where acquiring a result of an observation of an authoring user may be executed by, for example, the receiving module 110 of FIG. 1A. For example, an electronic message 150, which was composed and sent by the authoring user 130, may be received by the receiving module 110. Such an electronic message 150 may further include a result of an observation of one or more physical characteristics of the authoring user 130 that was made during or proximate to the composition of the electronic message.

In some implementations, such an observation of one or more physical characteristics may be made by employing a sensor 170 (e.g., an fNIR device). Such a sensor 170 may be used in order to measure or observe the brain activities of the authoring user 130. More particularly, the sensor 170 (e.g., fNIR device) may be used in order to measure the blood and/or oxygen flow in the brain of the authoring user 130 during or proximate to the composition of the electronic message 150. The observed brain activities of the authoring user 130 may have a distinct pattern, which may be associated with a particular mental state (this may be accomplished by using the population sampling technique previously described). As a result, the observations made by the sensor 170 (e.g., fNIR device) of the physical characteristics (e.g., brain activities) of the authoring user 130 may result in the linking of the observed physical characteristics (e.g., brain activities) of the authoring user 130 to a particular mental state or an "inferred mental state" by a mental state determination module 162. In some implementations, the result of the observation may be in the form of an inferred mental state of the authoring user 130. For these implementations, an inferred mental state may be any mental state that may be determined by, for example, a mental state determination module 162 based, at least in part, on data provided by a sensor 170 (e.g., fNIR device). In some embodiments, an inferred mental state may include, for example, preference, trust, fear, happiness, pain, distress, anger, deception, fair or unfairness, frustration, approval and disapproval, degree of attention, memory usage—both short and long term, and so forth, of the subject (e.g., authoring user 130).

The operational flow 200 may then move to another acquisition operation 204, where acquiring a result of an observation of a receiving user may be executed by, for example, a determination module 112 of FIG. 1A. For example, during or proximate to the presentation of the electronic message 150 to the receiving user 120, the determination module 112 may observe one or more physical characteristics of the receiving user 130 using one or more sensors 136 and/or one or more external sensors 138. In some implementations, the result of the observation may be in the form of an inferred mental state of the receiving user 130. For example, suppose the electronic message 150 is an IM message. As the IM message is being presented to and read by the receiving user 120, a sensor 136/138, such as a galvanic skin sensing device (which measures a change in the electrical resistance of a skin), may be used in order to measure changes in the electrical resistance of the skin of the receiving user 120 as the IM message is being read. Based, at least in part, on the measurement of the electrical resistance of the skin of the receiving user 120, an inferred mental state may be associated with the receiving user 120. For instance, a strong response (e.g., large changes in electrical resistance of the skin of the receiving user 120) may infer that the receiving user 120 is in a fearful or an angry state while a weak response (e.g, small changes in the electrical resistance of the skin of the receiving user 120) may infer that the receiving user 120 is in a relatively calm state as the receiving user 120 is reading the IM message.

The operational flow 200 may then move to a comparison operation 206, where comparing the result of the observation of the authoring user with the result of the observation of the receiving user may be executed by, for example, the comparison module 114 of FIG. 1A. For instance, in some implementations, the comparison module 114 may compare the inferred mental state of the authoring user 130 with the inferred mental state of the receiving user 120. For example, if the inferred mental state (e.g., happiness) of the authoring user 130 has been determined by a mental state determination module 141 or 162, and the mental state of the receiving user 120 has been determined by a mental state determination module 140, then the comparison module 114 may compare the inferred mental state of the receiving user 120 with the inferred mental state of the authoring user 130 in order to determine whether the inferred mental state of the receiving user 120 is similar to the inferred mental state (e.g., happiness) of the authoring user 130.

Finally, the operational flow 200 may then move to a presentation operation 208, where presenting data indicative of an extent of congruity between the result of the observation of the authoring user and the result of the observation of the receiving user based at least in part on said comparing may occur. For example, in some implementations, presenting data indicative of an extent of congruity (e.g., differences) between the result of the observation of the authoring user (e.g., as provided by the receiving module 110 or the authoring network device 104 of FIG. 1A) and the result of the observation of the receiving user based at least in part on said comparing (e.g., as provided by the determination module 112 of FIG. 1A) may be performed by a presentation module 118 of FIG. 1A. In some implementations, the extent of congruity may be the extent of congruity between an inferred mental state of the authoring user 130 during or proximate to the composition of the electronic message 150 and an inferred mental state of the receiving user 120 during or proximate to the display of the electronic message 150. Such a presentation may be made, in some implementations, to the receiving user 120 and/or to a third party network device 106 via the user interface 144, network communication interface 132, and/or email and/or IM application 134.

Figure 3:
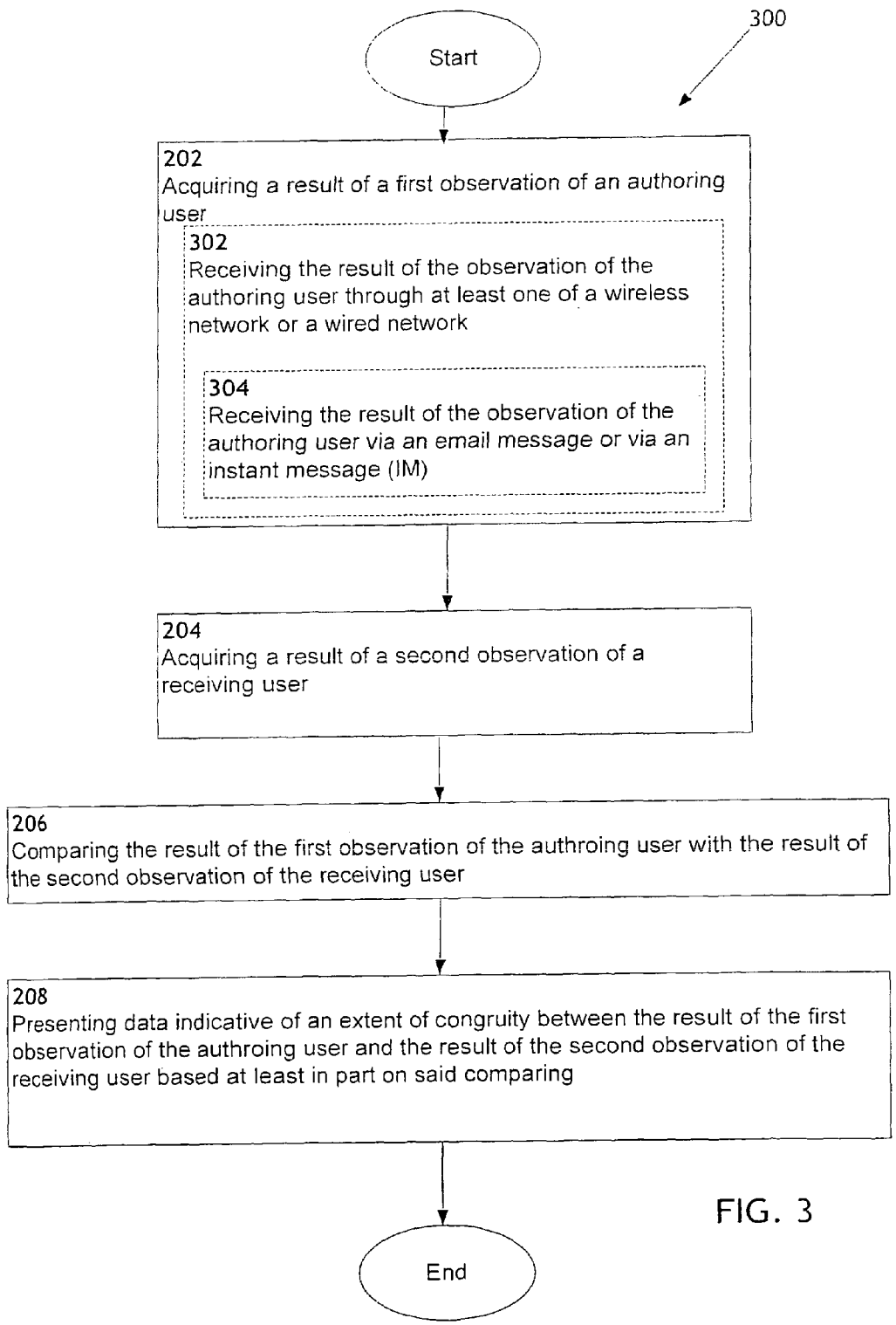
FIG. 3 is a high-level logic flowchart of a process depicting alternate implementations of the acquisition operation 202 of FIG. 2.

FIG. 3 illustrates various embodiments of the example acquisition operation 202 of FIG. 2. In particular, FIG. 3 illustrates example embodiments where the acquisition operation 202 may include at least one additional operation, operations 302 and/or 304. For instance, in some implementations, the acquisition operation 202 of FIG. 2 may include operation 302, which is a receiving operation for receiving the result of the observation of the authoring user through at least one of a wireless network or a wired network. For example, such an operation 302 may be implemented by a network device (e.g., receiving module 110 of receiving network device 102 of FIG. 1A) receiving the result of the observation of the authoring user (e.g., as provided by email and/or IM application 168 of authoring network device 104 of FIG. 1B) through at least one of a wireless network or a wired network.

Acquisition operation 202 may further include, for example, a receiving operation 304 for receiving the result of the observation of the authoring user via an email message or via an instant message (IM). For example, such an operation 304 may be implemented by a network device (e.g., receiving network device 102 of FIG. 1A) receiving (e.g., receiving module 110 of the receiving network device 102) the result of the observation (e.g., inferred mental state of the authoring user 130 provided by the mental state determination module 162 of authoring network device 104 of FIG. 1B) of the authoring user via an email message or via an IM (e.g., as provided by email and/or IM application 168 of authoring network device 104 of FIG. 1B).

Figure 4B:
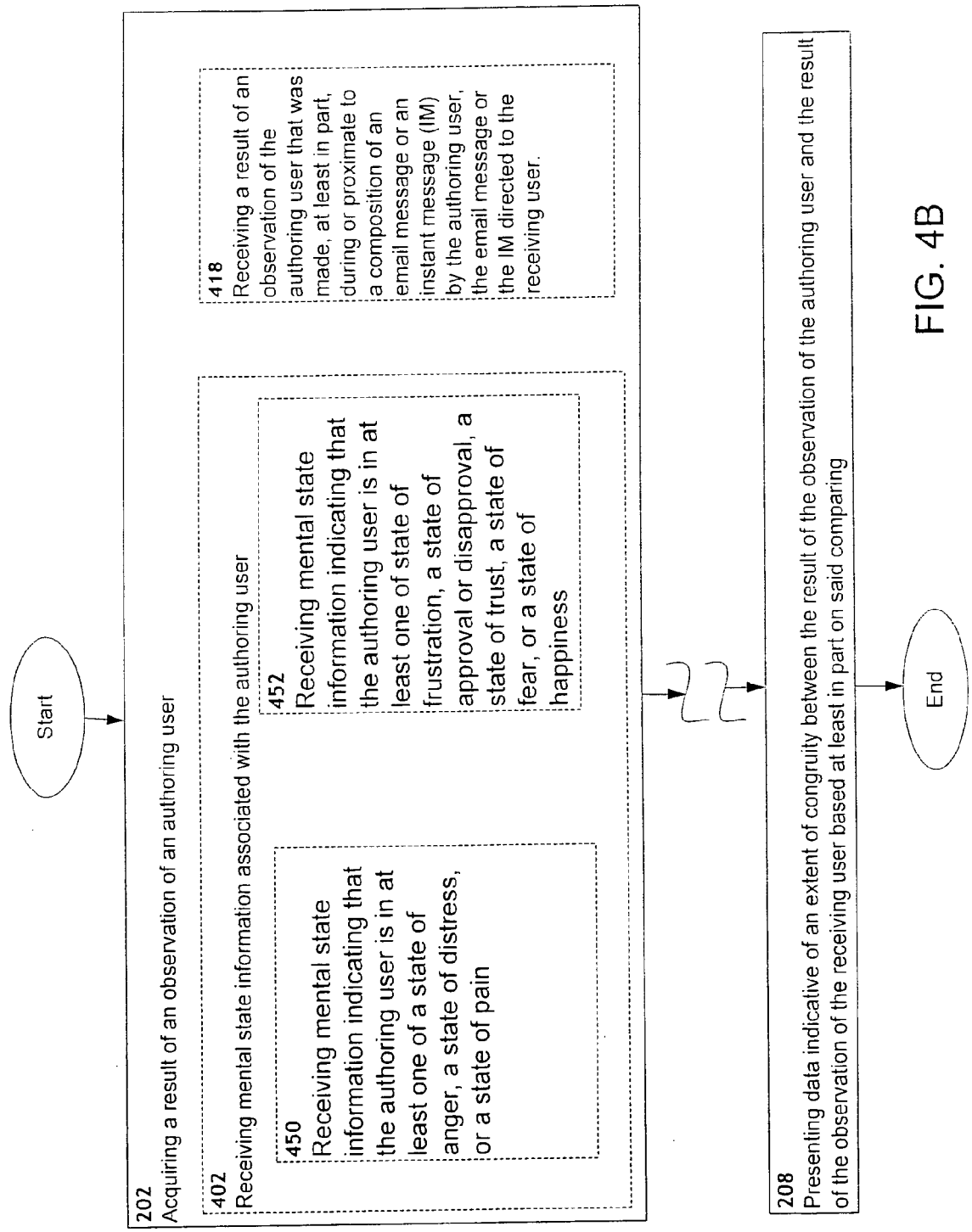
FIG. 4B is a high-level logic flowchart of a process depicting alternate implementations of the acquisition operation 202 of FIG. 2.

In some alternative embodiments or the same embodiments, the example acquisition operation 202 of FIG. 2 may include other additional operations, which may be executed by, for example, the receiving module 110 of FIG. 1A. Such additional operations may include, for example, operations 402, 406, 408, 410, 412, 414, 416, and/or 418 as illustrated in FIGS. 4A and 4B. For instance, in some implementations, the acquisition operation 202 may include a receiving operation 402 for receiving mental state information associated with the authoring user. For example, the receiving network device 102 of FIG. 1A receiving (e.g., via receiving module 110 and network communication interface 132) mental state information (e.g., an inferred mental state as provided by mental state determination module 162 of authoring network device 104 of FIG. 1B including, for example, anger, distress, frustration, trust, fear, and/or happiness) associated with the authoring user.

The receiving operation 402 may further include a mental state receiving operation 406 for receiving mental state information inferred from one or more sensed physical characteristics of the authoring user. For example, the receiving network device of FIG. 1A receiving (e.g., by receiving module 110) mental state information (e.g, that authoring user 130 is feeling happy) inferred (e.g, via mental state determination module 162) from one or more sensed physical characteristics of the authoring user (e.g., based upon voice stress as indicated by sensor 170 (e.g., a voice capture device)).

The mental state receiving operation 406 may include additional operations in various alternative implementations. For example, in one implementation, the mental state receiving operation 406 may include an operation 408 for receiving mental state information inferred from at least one of galvanic skin response, heart rate, blood pressure, or respiration associated with the authoring user. For example, the receiving network device of FIG. 1A receiving (e.g., via wireless and/or wired network 108) mental state information (e.g., that the authoring user 130 is feeling distressed) inferred (e.g., via mental state determination module 162) from at least one of galvanic skin response, heart rate, blood pressure, or respiration associated with the authoring user (e.g., obtained from one or more sensors 170 of FIG. 1B including, for example, a galvanic skin response device, a heart monitor, a blood pressure monitor, or a respiratory monitor).

In the same implementation or a different implementation, the receiving operation 406 may include an operation 410 for receiving mental state information inferred from at least one of facial expression, skin characteristic, voice characteristic, or iris dilation associated with the authoring user. For example, the receiving network device 102 of FIG. 1A receiving (e.g., receiving module 110) mental state information (e.g., authoring user 130 is "angry") inferred (e.g, by mental state determination module 162) from at least one of facial expression, skin characteristic, voice characteristic, or iris dilation associated with the authoring user (e.g., based on an output of sensor 170, which in some instances may be an image capture device and/or an audio capture device associated with authoring user 130).

In the same implementation or a different implementation, the receiving operation 406 may include an operation 412 for receiving mental state information inferred from at least one of blood oxygen or blood volume changes of a brain associated with the authoring user. For example, the receiving network device 102 of FIG. 1A receiving mental state information (e.g., that the authoring user 130 is fearful) inferred from (e.g., via mental state determination module 162 of authoring network device 104 of FIG. 1B) at least one of blood oxygen or blood volume changes of a brain associated with the authoring user (e.g., as measured by a sensor 170 associated with the authoring user 130 including, for example, an fMRI device).

In the same implementation or a different implementation, the receiving operation 406 may include an operation 414 for receiving mental state information associated with functional magnetic resonance imaging data. For example, the receiving network device 102 of FIG. 1A receiving (e.g., via receiving module 110) mental state information (e.g., that the authoring user 130 is frustrated) associated with functional magnetic resonance imaging data (e.g., using sensor 170 associated with the authoring user 130 including, for example, an fMRI device).

In the same implementation or a different implementation, the receiving operation 406 may include an operation 416 for receiving mental state information associated with functional near infrared data. For example, the receiving network device 102 of FIG. 1A receiving (e.g., via the electronic message 150) mental state information (e.g., that the authoring user 130 is in a state of pain) associated with functional near infrared data (e.g., using sensor 170 associated with the authoring user 130 including, for example, an fNIR device).

FIG. 4B illustrates certain embodiments of operation 402 of FIG. 4A. In particular, FIG. 4B illustrates embodiments where operation 402 may include additional operation 450 and/or operation 452. For instance, in some implementations, operation 402 includes operation 450 for receiving mental state information indicating that the authoring user is in at least one of a state of anger, a state of distress, or a state of pain. For example, the receiving network device 102 of FIG. 1A receiving (e.g., via receiving module 110) mental state information (e.g., as provided by mental state determination module 162 of authoring network device 104) indicating that the authoring user is in at least one of state of anger, a state of distress, or a state of pain (e.g., based on data provided by a sensor 170 such as, for example, an fMRI device).

In the same implementations or alternative implementations, operation 402 may also include operation 452 for receiving mental state information indicating that the authoring user is in at least one of a state of frustration, a state of approval or disapproval, a state of trust, a state of fear, or a state of happiness. For example, the receiving network device 102 of FIG. 1A receiving (e.g., via wireless and/or wired network 108) mental state information (e.g., as provided by mental state determination module 162 of authoring network device 104) indicating that the authoring user is in at least one of state of frustration, a state of approval or disapproval, a state of trust, a state of fear, or a state of happiness (e.g., based on data provided by a sensor 170 such as, for example, an fNIR device).

FIG. 4B also shows that in some embodiments, the acquisition operation 202 of FIG. 2 may include an operation 418 for receiving a result of an observation of the authoring user that was made, at least in part, during or proximate to a composition of an email message or an instant message (IM) by the authoring user, the email message or the IM directed to the receiving user. For example, the receiving network device 102 of FIG. 1A receiving (e.g., via receiving module 110) a result of an observation (e.g., made by determination module 160 of authoring network device 160 of FIG. 1B) of the authoring user that was made (e.g., by using a sensor 170 associated with the authoring user 130 including, for example, a galvanic skin sensor device), at least in part, during or proximate to a composition of an email message or an instant message (IM) by the authoring user, the email message or the IM directed to the receiving user (e.g., via wireless and/or wired network or networks 108).

Figure 5A:
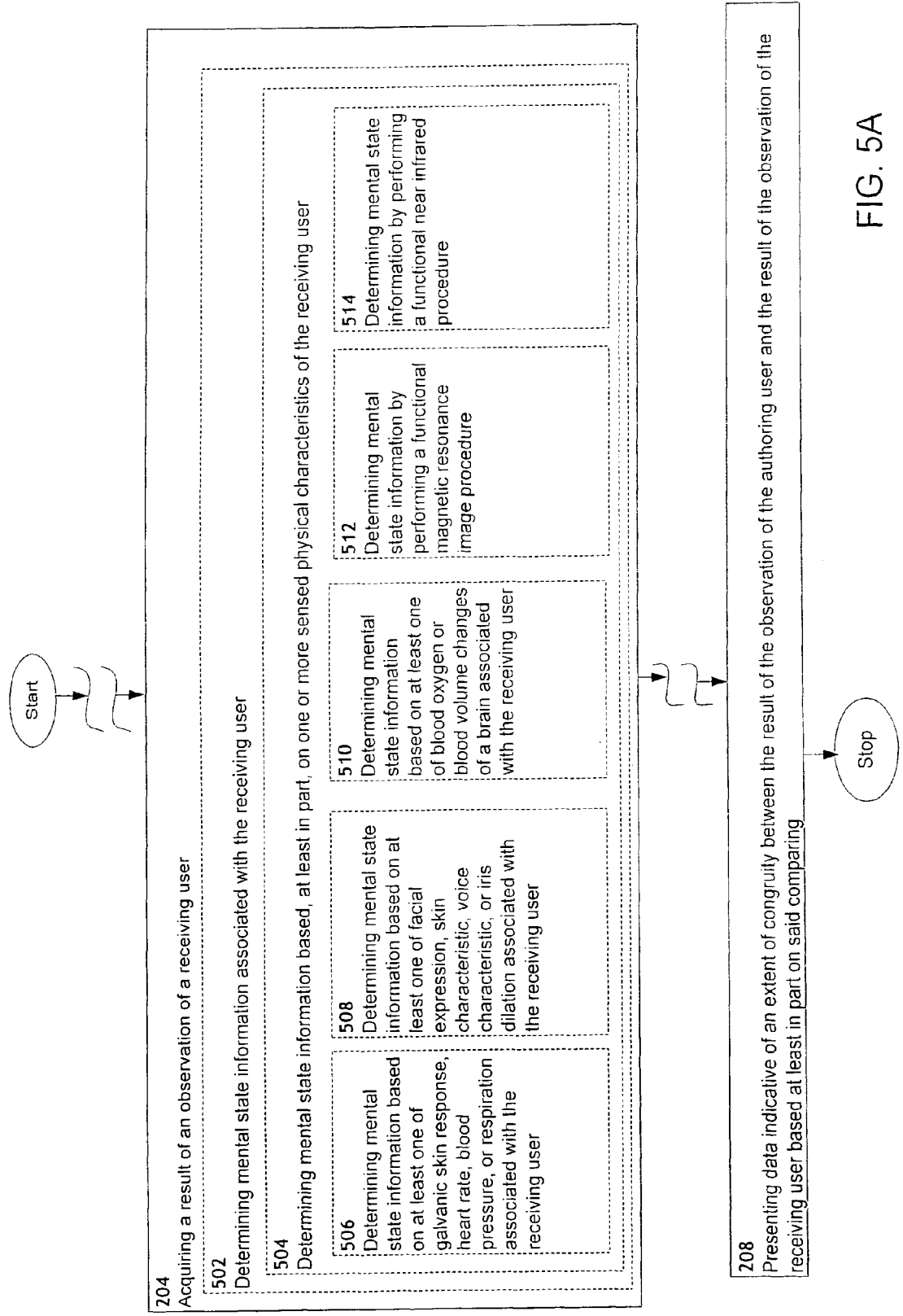
FIG. 5A is a high-level logic flowchart of a process depicting alternate implementations of acquisition operation 204 of FIG. 2.

FIG. 5A illustrates certain embodiments of the example acquisition operation 204 of FIG. 2. In particular, FIG. 5A illustrates example embodiments where the acquisition operation 204 of FIG. 2 may include one or more additional operations, which may be executed by the determination module 112 of FIG. 1 in some implementations. These additional operations include, for example, operations 502, 504, 506, 508, 510, 512, and/or 514 as illustrated in FIG. 5A. For instance, the acquisition operation 204 of FIG. 2 may include operation 502, which is an operation for determining mental state information associated with the receiving user. For example, the receiving network device 102 of FIG. 1A determining (e.g., using mental state determination module 140) mental state information (e.g., that indicates, for example, that the receiving user 120 is angry) associated with the receiving user.

In some implementations, operation 502 may further include operation 504, which is an operation for determining mental state information based, at least in part, on one or more sensed physical characteristics of the receiving user. For example, the one or more physical characteristics of receiving user 130 of FIG. 1A may be sensed using one or more sensors 136/138 including, for example, an fNIR device, an fMRI device, an MEG device, an EEG device, and so forth. In some implementations, the operation 504 for determining mental state information may further include additional one or more operations.

For instance, in some implementations, operation 504 may include an operation 506 for determining mental state information based on at least one of galvanic skin response, heart rate, blood pressure, or respiration associated with the receiving user. For example, the receiving network device 102 of FIG. 1A determining (e.g., via mental state determination module 112) mental state information (e.g., that indicates that the receiving user 120, for example, is distressed) based on at least one of galvanic skin response, heart rate, blood pressure, or respiration associated with the receiving user (e.g., as measured by using sensors 136 and/or 138, where sensors 136 and/or 138 may include at least a galvanic skin response device, a heart monitor, a blood pressure monitor, or a respiratory monitor).

In the same implementation or in alternative implementations, operation 504 may include an operation 508 for determining mental state information based on at least one of facial expression, skin characteristic, voice characteristic, or iris dilation associated with the receiving user. For example, the receiving network device 102 of FIG. 1A determining (e.g., via mental state determination module 140) mental state information (e.g., that indicates, for example, that the receiving user 120 is in pain) based on at least one of facial expression, skin characteristic, voice characteristic, or iris dilation (e.g., as detected by using sensors 136 and/or 138, where sensors 136 and/or 138 may include an image capture device for capturing facial expressions, a galvanic skin response device, an audio capturing device for detecting voice characteristics, or an iris tracking device for detecting iris dilation) associated with the receiving user 120.

Operation 504 may also include an operation 510 for determining mental state information based on at least one of blood oxygen or blood volume changes of a brain associated with the receiving user. For example, the receiving network device 102 of FIG. 1A determining (e.g., via mental state determination module 142) mental state information (e.g., that indicates, for example, that the receiving user 120 is frustrated) based on at least one of blood oxygen or blood volume changes of a brain (e.g., as measured by a sensor 136/138 such as an fMRI device or an fNIR device) associated with the receiving user.

In some implementations, operation 504 may include an operation 512 for determining mental state information by performing a functional magnetic resonance image procedure. For example, such a functional magnetic resonance image procedure may include, for example, the use of a sensor 136/138 including, for example, an fMRI device to scan or resonate a subject's brain (e.g., receiving user 120).

Operation 504 in some implementations may also include an operation 514 for determining mental state information by performing a functional near infrared procedure. For example, such a functional near infrared procedure may include, for example, the use of a sensor 136/138 including, for example, an fNIR device on a subject's brain (e.g., receiving user 120).

Figure 5B:
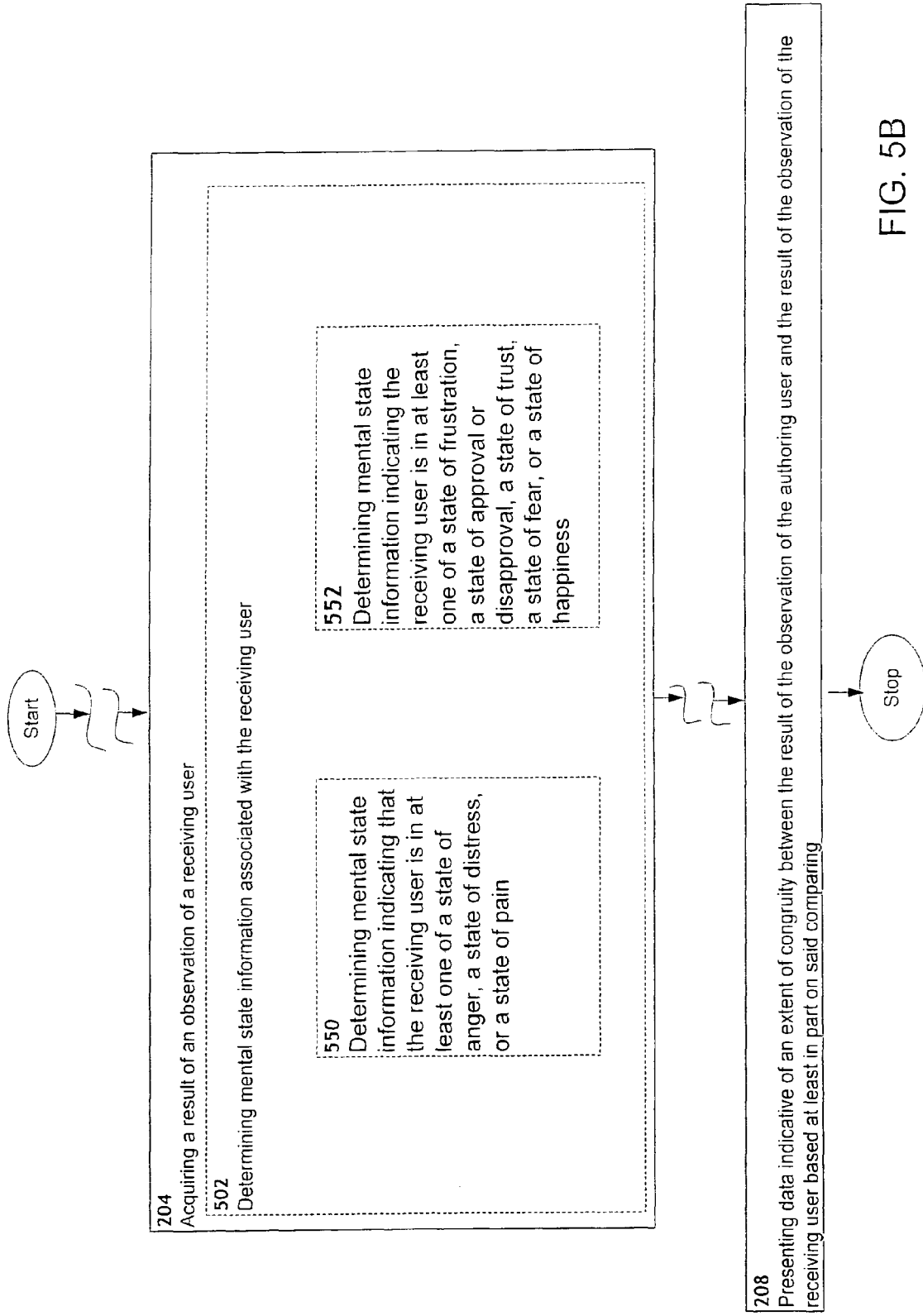
FIG. 5B is a high-level logic flowchart of a process depicting alternate implementations of acquisition operation 204 of FIG. 2.

FIG. 5B illustrates certain embodiments of operation 502 of FIG. 5A. In particular, FIG. 5B illustrates embodiments where operation 502 may include additional operation 550 and/or operation 552. For instance, in some implementations, operation 502 includes operation 550 for determining mental state information indicating that the receiving user is in at least one of a state of anger, a state of distress, or a state of pain. For example, the receiving network device 102 using the determination module 112 determining (e.g., via mental state determination module 140) mental state information indicating that the receiving user is in at least one of a state of anger, a state of distress, or a state of pain (e.g., based on data provided by one or more sensors 136/138 including, for example, an iris response device, a gaze tracking device, a skin response device (e.g., galvanic skin sensor), and/or a voice response device).

In the same implementation or alternative implementation, operation 502 may also include operation 552 for determining mental state information indicating that the receiving user is in at least one of a state of frustration, a state of approval or disapproval, a state of trust, a state of fear, or a state of happiness. For example, the receiving network device 102 using the determination module 112 determining (e.g., via mental state determination module 140) mental state information indicating that the receiving user is in at least one of a state of frustration, a state of approval or disapproval, a state of trust, a state of fear, or a state of happiness (e.g., based on data provided by one or more sensors 136/138 including, for example, an fMRI device and/or an fNIR device).

Figure 6:
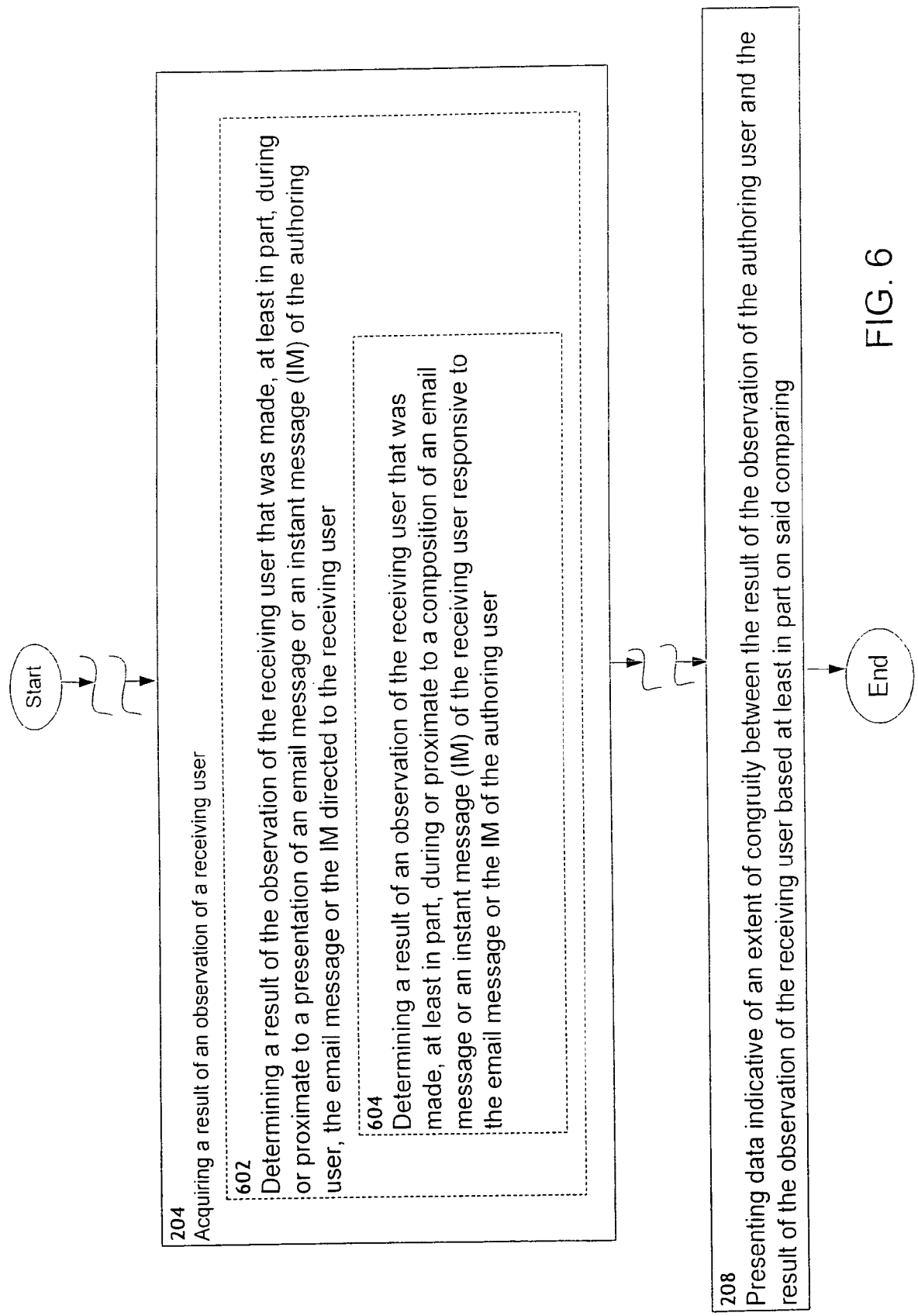
FIG. 6 is a high-level logic flowchart of a process depicting alternate implementations of acquisition operation 204 of FIG. 2.

In some alternative implementations or in the above same implementations, the example acquisition operation 204 of FIG. 2 may include other additional operations such as operations 602 and/or 604 as illustrated in FIG. 6, which may also be executed by the determination module 112 of FIG. 1A. For example, in some implementations, operation 204 of FIG. 2 may include an operation 602 for determining a result of the observation of the receiving user that was made, at least in part, during or proximate to a presentation of an email message or an instant message (IM) of the authoring user, the email message or the IM directed to the receiving user. For example, the determination module 112 may determine the result of the observation (e.g., based on data provided by one or more sensors 136/138) of the receiving user that was made, at least in part, during or proximate to a presentation of an email message or an instant message (IM) of the authoring user 130 (e.g., received through the wireless and/or wired network or networks 108), the email message or the IM directed (e.g., sent) to the receiving user 120.

In some implementations, operation 602 may further include an operation 604 for determining a result of an observation of the receiving user that was made, at least in part, during or proximate to a composition of an email message or an instant message (IM) of the receiving user responsive to the email message or the IM of the authoring user. For example, the determination module 112 may determine a result of an observation (e.g., based on data provided by one or more sensors 136/138 including, for example, an fNIR device and/or fMRI device) of the receiving user that was made, at least in part, during or proximate to a composition of an email message or an instant message (e.g., received through the wireless and/or wired network or networks 108) of the receiving user 120 responsive to the email message or the IM of the authoring user 130.

Figure 7:
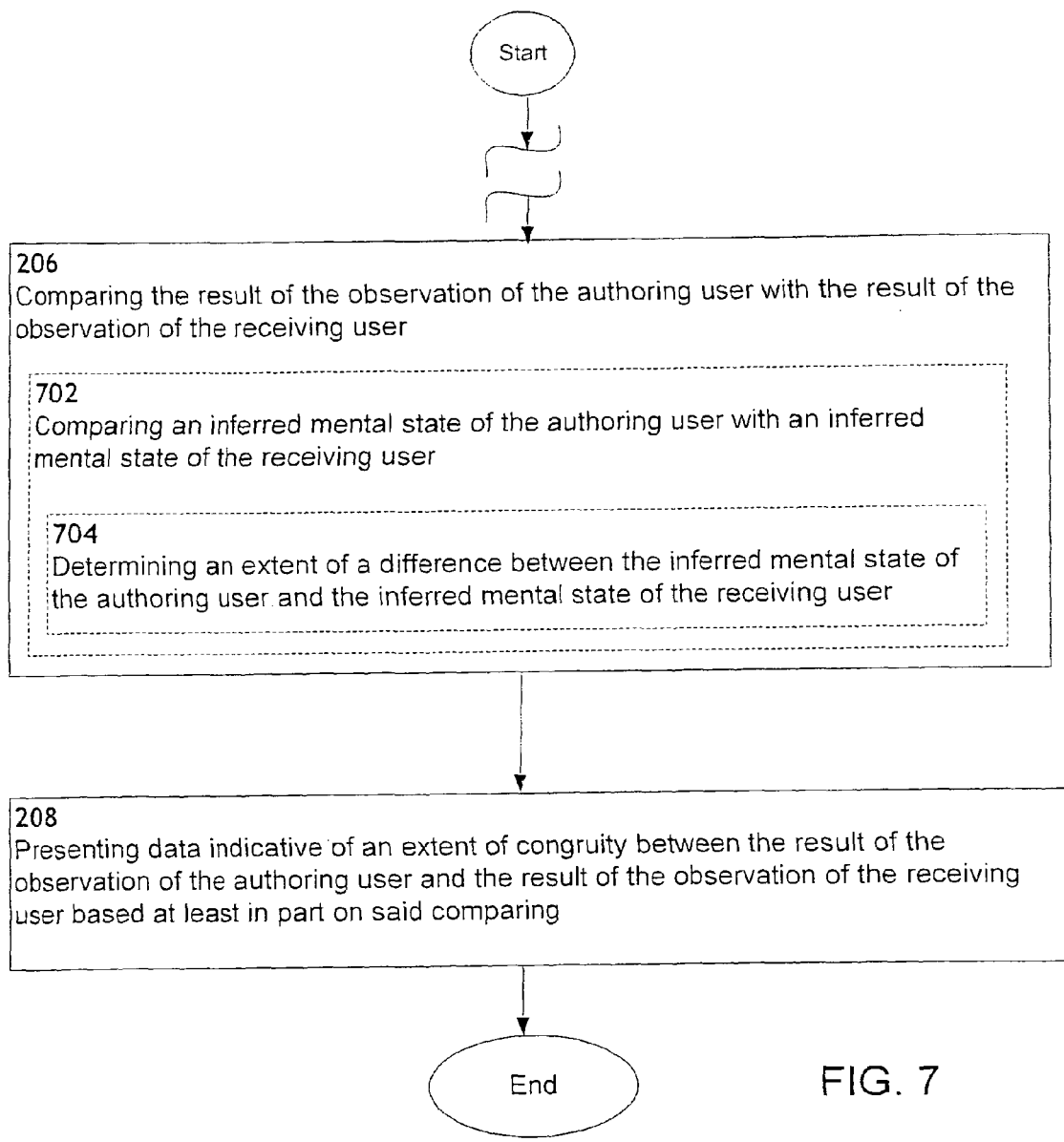
FIG. 7 is a high-level logic flowchart of a process depicting alternate implementations of comparison operation 206 of FIG. 2.

FIG. 7 illustrates various embodiments of the comparison operation 206 of FIG. 2. More particularly, FIG. 7 illustrates example embodiments where the comparison operation 206 of FIG. 2 may include one or more additional operations including, for example, operations 702 and/or 704, which may be executed by, in some instances, the comparison module 114 of FIG. 1A. For example, the comparison operation 206 of FIG. 2 may include operation 702, which is an operation for comparing an inferred mental state of the authoring user with an inferred mental state of the receiving user. For example, the comparison module 114 of the receiving network device 102 comparing an inferred mental state (e.g., inferred angry state) of the authoring user 130 with an inferred mental state (e.g., inferred happy state) of the receiving user 120.

In some implementations, operation 702 may further include an additional operation 704 for determining an extent of a difference between the inferred mental state of the authoring user and the inferred mental state of the receiving user. For example, the comparison module 114 of the receiving network device 102 determining an extent of a difference between the inferred mental state (e.g., inferred trustful state) of the authoring user and the inferred mental state (e.g., inferred fearful state) of the receiving user 120.

Figure 8:
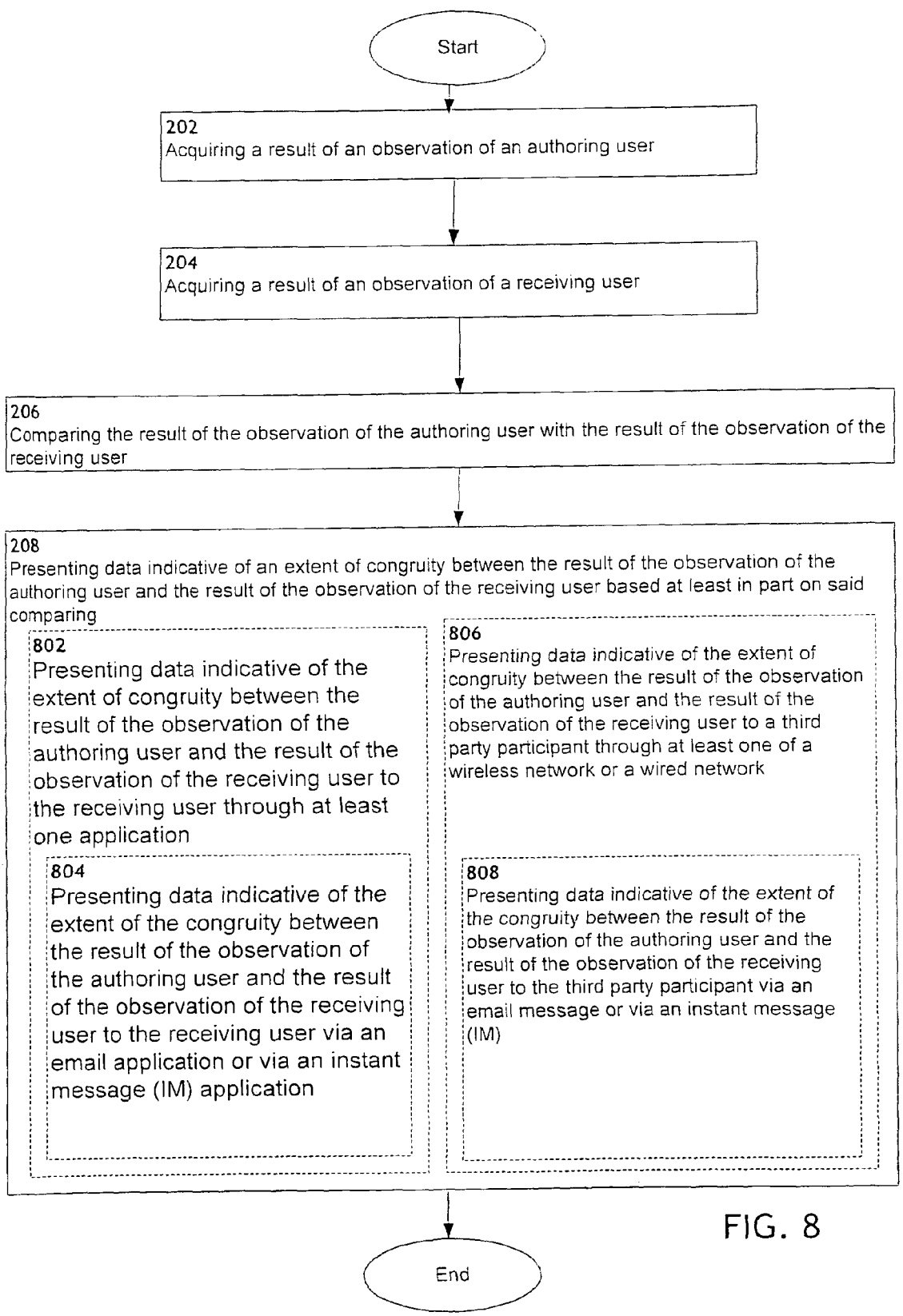
FIG. 8 is a high-level logic flowchart of a process depicting alternate implementations of presentation operation 208 of FIG. 2.

FIG. 8 illustrates various embodiments of the presentation operation 208 of FIG. 2. More particularly, FIG. 8 illustrates example embodiments where the presentation operation 208 of FIG. 2 may include one or more additional operations including, for example, operations 802, 804, 806, and/or 808, which may be executed by, in some instances, the presentation module 118 of FIG. 1A. As described above, in some implementations, the presentation operation 208 of FIG. 2 may include operation 802, which is an operation for presenting data indicative of the extent of congruity between the result of the observation of the authoring user and the result of the observation of the receiving user to the receiving user through at least one application. For example, the presentation module 118 via the user interface 144 and/or via the network communication interface 132 presenting data indicative of the extent of congruity between the result of the observation (e.g., by sensor 170 including, for example, an fMRI device) of the authoring user 130 and the result of the observation (e.g., by sensor 136/138 including, for example, an fMRI device) of the receiving user 120 to the receiving user 120 through at least one application 134.

In some instances, such an operation 802 may include an operation 804 for presenting data indicative of the extent of the congruity between the result of the observation of the authoring user and the result of the observation of the receiving user to the receiving user via an email application or via an instant message (IM) application. For example, the presentation module 118 via the user interface 144 presenting data indicative of the extent of the congruity between the result of the observation (e.g., based at least in part on data provided by determination module 160 of authoring network device 104 of FIG. 1B) of the authoring user 130 and the result of the observation (e.g, based at least in part on data provided by the determination module 112 of the receiving network device 102) of the receiving user 120 to the receiving user 120 via an email application or via an instant message (IM) application.

The presentation operation 208 of FIG. 2 may, in some instances, also include an operation 806 for presenting data indicative of the extent of congruity between the result of the observation of the authoring user and the result of the observation of the receiving user to a third party participant through at least one of a wireless network or a wired network. For example, the presentation module 118 of FIG. 1A presenting (e.g., via the network communication interface 132) data indicative of the extent of congruity between the result of the observation (e.g., inferring that the authoring user 130 is in a, for example, state of frustration) of the authoring user 130 and the result of the observation (e.g., inferring that the receiving user 120 is in a, for example, state of happiness) of the receiving user 120 to a third party participant 106 through at least one of a wireless network or a wired network 108.

For these embodiments, operation 806 may also include an operation 808 for presenting data indicative of the extent of the congruity between the result of the observation of the authoring user and the result of the observation of the receiving user to the third party participant via an email message or via an instant message (IM). For example, the presentation module 118 of FIG. 1A presenting (e.g., via the network communication interface 132) data indicative of the extent of the congruity between the result of the observation (e.g., inferring that the authoring user 130 is in a, for example, state of anger) of the authoring user and the result of the observation (e.g., inferring that the receiving user 120 is in a, for example, state of distress) of the receiving user 120 to the third party participant or device 106 via an email message or via an instant message (IM).

Figure 9:
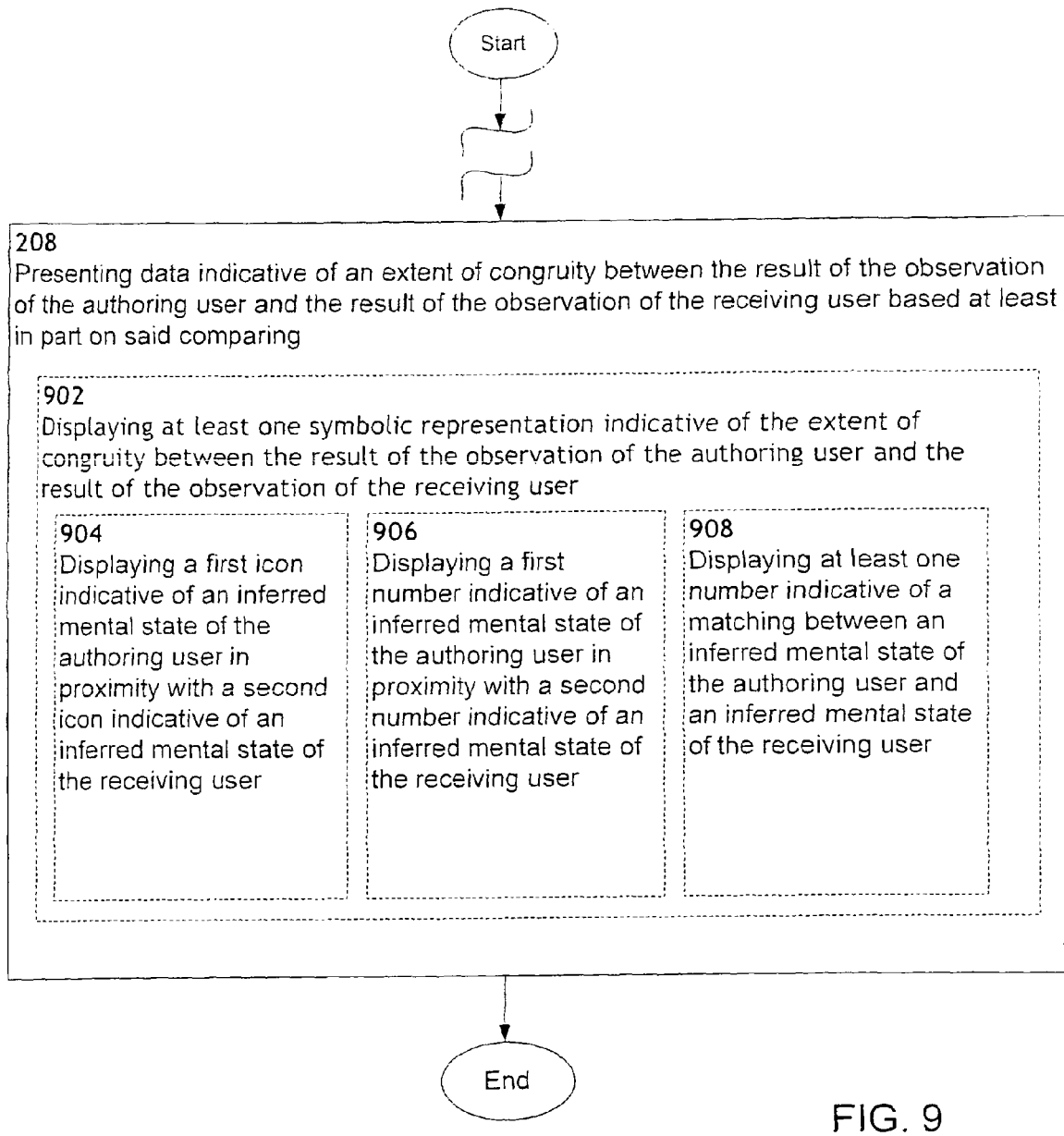
FIG. 9 is a high-level logic flowchart of a process depicting alternate implementations of presentation operation 208 of FIG. 2.

In some alternative implementations or in the same above implementations, the example presentation operation 208 of FIG. 2 may include other additional operations such as operations 902, 904, 906, and/or 908 as illustrated in FIG. 9, which may also be executed by the presentation module 118 of FIG. 1A. For instance, in some implementations, presentation operation 208 of FIG. 2 may include an operation 902 for displaying at least one symbolic representation indicative of the extent of congruity between the result of the observation of the authoring user and the result of the observation of the receiving user. For example, the presentation module 118 of FIG. 1A displaying (e.g., via the user interface and/or via the network communication interface 132) at least one symbolic representation indicative of the extent of congruity between the result of the observation (e.g., as provided by sensor or sensors 170 including, for example, an fMRI device and/or an fNIR device) of the authoring user 130 and the result of the observation (e.g., as provided by sensor or sensors 136/138 including, for example, an fMRI device and/or an fNIR device) of the receiving user 120.

For these implementations, the operation 902 may also include operation 904 for displaying a first icon indicative of an inferred mental state of the authoring user in proximity with a second icon indicative of an inferred mental state of the receiving user. For example, the presentation module 118 of FIG. 1A displaying (e.g., via a remote or an integrated display monitor) a first icon indicative of an inferred mental state (e.g., inferring that the authoring user 130 is in a, for example, state of frustration) of the authoring user 130 in proximity with a second icon indicative of an inferred mental state (e.g., inferring that the receiving user 120 is in a, for example, state of frustration) of the receiving user 120.

In the same implementations or in alternative implementations, operation 902 may also include operation 906 for displaying a first number indicative of an inferred mental state of the authoring user in proximity with a second number indicative of an inferred mental state of the receiving user. For example, the presentation module 118 of FIG. 1A displaying (e.g., via a remote or an integrated display monitor) a first number indicative of an inferred mental state (e.g., inferring that the authoring user 130 is in a, for example, state of happiness) of the authoring user in proximity with a second number indicative of an inferred mental state (e.g., inferring that the receiving user 120 is in a, for example, state of happiness) of the receiving user 120.

In still the same implementations or in alternative implementations, operation 902 may further include operation 908 for displaying at least one number indicative of a matching between an inferred mental state of the authoring user and an inferred mental state of the receiving user. For example, the presentation module 118 of FIG. 1A displaying (e.g., via a remote or an integrated display monitor) at least one number indicative of a matching between an inferred mental state (e.g., inferring that the authoring user 130 is in a, for example, state of frustration) of the authoring user 130 and an inferred mental state (e.g., inferring that the receiving user 120 is in a, for example, state of frustration) of the receiving user 120.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those of ordinary skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A system, comprising:
 a determination module configured to determine a result of an observation of a receiving user based at least in part on received sensor data indicative of one or more physiological characteristics of the receiving user, wherein the determination module is configured to determine a result that includes at least an inferred mental state associated with the receiving user inferred based at least in part on the received sensor data indicative of one or more physiological characteristics of the receiving user at least one of during or proximate to a time of a display of an electronic message to the receiving user;
 a receiving module configured to receive a result of an observation of an authoring user, wherein the receiving module is configured to receive a result that includes at least data indicative of an inferred mental state of the authoring user that was inferred based at least in part on one or more sensed physiological characteristics of the authoring user that were sensed at least one of during or proximate to a time of an authoring of the electronic message; and
 a comparison module operatively coupled to the receiving module and the determination module and configured to compare the result of the observation of the receiving user with the result of the observation of the authoring user for providing at least an indication of a congruity between the inferred mental state of the receiving user and the inferred mental state of the authoring user with respect to the electronic message; and
 wherein at least one of the determination module, the receiving module, or the comparison module is at least partly implemented in hardware.

2. The system of claim 1 further comprising:
 one or more sensors configured to sense one or more physiological characteristics of the receiving user.

3. The system of claim 2, wherein said one or more sensors configured to sense one or more physiological characteristics of the receiving user comprise:
 at least one of a galvanic skin sensor device, a heart rate sensor device, a blood pressure sensor device, or a respiration sensor device.

4. The system of claim 2, wherein said one or more sensors configured to sense one or more physiological characteristics of the receiving user further comprise:
 at least one of a facial expression sensor device, a skin characteristic sensor device, a voice response device, a gaze tracking device, or an iris response device.

5. The system of claim 2, wherein said one or more sensors configured to sense one or more physiological characteristics of the receiving user are further configured to:
 sense at least one of blood oxygen or blood volume changes of a brain associated with the receiving user.

6. The system of claim 1, wherein said determination module configured to determine a result of an observation of a receiving user based at least in part on received sensor data indicative of one or more physiological characteristics of the receiving user, wherein the determination module is configured to determine a result that includes at least an inferred mental state associated with the receiving user inferred based at least in part on the received sensor data indicative of one or more physiological characteristics of the receiving user at least one of during or proximate to a time of a display of an electronic message to the receiving user comprises:
 a mental state determination module.

7. The system of claim 6, wherein said mental state determination module comprises:
 a mental state determination module configured to infer a mental state associated with the receiving user based, at least in part, on received sensor data indicative of one or more physiological characteristics of the receiving user.

8. The system of claim 1, wherein said receiving module configured to receive a result of an observation of an authoring user, wherein the receiving module is configured to receive a result that includes at least data indicative of an inferred mental state of the authoring user that was inferred based at least in part on one or more sensed physiological characteristics of the authoring user that were sensed at least one of during or proximate to a time of an authoring of the electronic message comprises:
 a mental state determination module configured to receive data indicative of a mental state associated with the authoring user and inferred from one or more sensed physiological characteristics of the authoring user.

9. The system of claim 1, wherein said receiving module configured to receive a result of an observation of an authoring user, wherein the receiving module is configured to receive a result that includes at least data indicative of an inferred mental state of the authoring user that was inferred based at least in part on one or more sensed physiological characteristics of the authoring user that were sensed at least one of during or proximate to a time of an authoring of the electronic message comprises:

a mental state determination module configured to infer a mental state associated with the authoring user based, at least in part, on the received result of the observation of the authoring user.

10. The system of claim 1, wherein said comparison module operatively coupled to the receiving module and the determination module and configured to compare the result of the observation of the receiving user with the result of the observation of the authoring user for providing at least an indication of a congruity between the inferred mental state of the receiving user and the inferred mental state of the authoring user with respect to the electronic message comprises:
an inferred mental state comparison module.

11. The system of claim 10, wherein said inferred mental state comparison module comprises:
an inferred mental state module configured to compare an inferred mental state associated with the authoring user and an inferred mental state associated with the receiving user, the mental state associated with the authoring user inferred from the observation of the authoring user and the mental state associated with the receiving user inferred from the observation of the receiving user.

12. The system of claim 1, further comprising:
a presentation module operatively coupled to the comparison module.

13. The system of claim 12, wherein said presentation module operatively coupled to the comparison module comprises:
a presentation module configured to present data indicative of an extent of congruity between the result of the observation of the authoring user and the result of the observation of the receiving user responsive at least in part to the comparison module operatively coupled to the receiving module and the determination module and configured to compare the result of the observation of the receiving user with the result of the observation of the authoring user for providing at least an indication of a congruity between the inferred mental state of the receiving user and the inferred mental state of the authoring user with respect to the electronic message.

14. The system of claim 12, wherein said presentation module operatively coupled to the comparison module comprises:
a presentation module configured to present data indicative of an extent of congruity between an inferred mental state associated with the authoring user and an inferred mental state associated with the receiving user, the mental state associated with the authoring user inferred from the observation of the authoring user and the mental state associated with the receiving user inferred from the observation of the receiving user.

15. The system of claim 1, further comprising:
a user interface.

16. The system of claim 15, wherein said user interface comprises:
at least one of a user display, a touch screen, a keypad, or a speaker system.

17. The system of claim 1, further comprising:
a network communication interface.

18. The system of claim 17, wherein said network communication interface comprises:
a network communication interface configured to interface with at least one of a wireless network or a wired network.

19. The system of claim 1, further comprising at least one of:
an email application; or
an instant message (IM) application.

20. The system of claim 2, wherein said one or more sensors configured to sense one or more physiological characteristics of the receiving user comprise at least one of:
a functional magnetic resonance imaging (fMRI) device; or
a functional near infrared (fNIR) device.

21. The system of claim 1 further comprising a network communication interface and wherein said receiving module configured to receive a result of an observation of an authoring user, wherein the receiving module is configured to receive a result that includes at least data indicative of an inferred mental state of the authoring user that was inferred based at least in part on one or more sensed physiological characteristics of the authoring user that were sensed at least one of during or proximate to a time of an authoring of the electronic message comprises:
a receiving module configured to receive a result of an observation of an authoring user at least partly via said network communication interface.

22. A computationally-implemented method, comprising:
determining a result of an observation of a receiving user based at least in part on received sensor data indicative of one or more physiological characteristics of the receiving user, the determining including at least determining a result that includes at least an inferred mental state associated with the receiving user inferred based at least in part on the received sensor data indicative of one or more physiological characteristics of the receiving user at least one of during or proximate to a time of a display of an electronic message to the receiving user;
receiving a result of an observation of an authoring user, the result including at least data indicative of an inferred mental state of the authoring user that was inferred based at least in part on one or more sensed physiological characteristics of the authoring user that were sensed at least one of during or proximate to a time of an authoring of the electronic message; and
comparing the result of the observation of the receiving user with the result of the observation of the authoring user for providing at least an indication of a congruity between the inferred mental state of the receiving user and the inferred mental state of the authoring user with respect to the electronic message; and
wherein at least one of the determining, the receiving, or the comparing is at least partly performed with one or more processing devices.

23. A system, comprising:
circuitry for determining a result of an observation of a receiving user based at least in part on received sensor data indicative of one or more physiological characteristics of the receiving user, the circuitry for determining configured to determine a result that includes at least an inferred mental state associated with the receiving user inferred at least partly from the received sensor data indicative of one or more physiological characteristics of the receiving user at least one of during or proximate to a time of a display of an electronic message to the receiving user;
circuitry for receiving a result of an observation of an authoring user, the circuitry for receiving configured to receive a result that includes at least data indicative of an inferred mental state of the authoring user that was inferred based at least in part on one or more sensed physiological characteristics of the authoring user that were sensed at least one of during or proximate to a time of an authoring of the message; and circuitry for comparing the result of the observation of the receiving user with the result of the observation of the authoring user for providing at least an indication of a congruity between the inferred mental state of the receiving user and the inferred mental state of the authoring user with respect to the electronic message.

\* \* \* \* \*